(12) United States Patent
Yoshizawa et al.

(10) Patent No.: US 12,114,964 B2
(45) Date of Patent: Oct. 15, 2024

(54) BIOLOGICAL INFORMATION MEASURING APPARATUS, NON-TRANSITORY COMPUTER-READABLE RECORDING MEDIUM HAVING STORED THEREIN A PROGRAM FOR CAUSING A COMPUTER TO EXECUTE A PROCESS FOR MEASURING BIOLOGICAL INFORMATION, AND METHOD FOR MEASURING BIOLOGICAL INFORMATION

(71) Applicant: TOHOKU UNIVERSITY, Sendai (JP)

(72) Inventors: Makoto Yoshizawa, Sendai (JP); Norihiro Sugita, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 1125 days.

(21) Appl. No.: 16/883,387

(22) Filed: May 26, 2020

(65) Prior Publication Data
US 2020/0288996 A1     Sep. 17, 2020

Related U.S. Application Data

(63) Continuation of application No. PCT/JP2018/043004, filed on Nov. 21, 2018.

(30) Foreign Application Priority Data

Nov. 30, 2017  (JP) .................. 2017-230362

(51) Int. Cl.
*A61B 5/021*    (2006.01)
*A61B 5/00*     (2006.01)
(Continued)

(52) U.S. Cl.
CPC ...... *A61B 5/02116* (2013.01); *A61B 5/02416* (2013.01); *A61B 5/347* (2021.01);
(Continued)

(58) Field of Classification Search
None
See application file for complete search history.

(56) References Cited

U.S. PATENT DOCUMENTS 6,261,235 B1  7/2001  Amano et al.
6,364,842 B1  4/2002  Amano et al.
(Continued)

FOREIGN PATENT DOCUMENTS

JP    7-136139 A     5/1995
JP    2003-47601 A   2/2003
(Continued)

OTHER PUBLICATIONS

N. Sugita, K. Obara, M. Yoshizawa, M. Abe, A. Tanaka and N. Homma, "Techniques for estimating blood pressure variation using video images," 2015 37th Annual International Conference of the IEEE Engineering in Medicine and Biology Society (EMBC), Milan, Italy, 2015, pp. 4218-4221 (Year: 2015).*
(Continued)

*Primary Examiner* — Benjamin S Melhus
*Assistant Examiner* — Samuel C Kim
(74) *Attorney, Agent, or Firm* — Myers Wolin, LLC

(57) ABSTRACT

A biological information measuring apparatus includes a distortion calculating unit that calculates, based on video pulse wave information representing a video pulse wave expressing a temporal change in a brightness value included in a video signal of a predetermined part of a subject, a waveform distortion obtained from a heartbeat basic component containing a frequency component of a heartbeat frequency band corresponding to a heart rate of the subject and a heartbeat high-frequency component related to a waveform of a pulse wave and containing a frequency component of a frequency band higher than the heartbeat frequency band, the heartbeat basic component and the
(Continued)

heartbeat high-frequency component being included in the video pulse wave; and a measuring unit that measures a fluctuation in a blood pressure of the subject based on the waveform distortion calculated by the distortion calculating unit.

6 Claims, 15 Drawing Sheets

(51) Int. Cl.
    *A61B 5/024*     (2006.01)
    *A61B 5/347*     (2021.01)
    *A61B 5/374*     (2021.01)
(52) U.S. Cl.
    CPC ............ *A61B 5/374* (2021.01); *A61B 5/7257* (2013.01); *A61B 5/7278* (2013.01); *A61B 5/7435* (2013.01)

(56) References Cited

U.S. PATENT DOCUMENTS

| | | | |
|---|---|---|---|
| 6,428,481 B1* | 8/2002 | Inukai | A61B 5/02225 600/500 |
| 2002/0065471 A1 | 5/2002 | Amano et al. | |
| 2002/0183627 A1 | 12/2002 | Nishii et al. | |
| 2015/0287187 A1* | 10/2015 | Redtel | G06T 7/0016 382/128 |
| 2016/0038044 A1* | 2/2016 | Banerjee | A61B 5/02116 600/480 |
| 2016/0051201 A1* | 2/2016 | Maani | A61B 5/7278 600/301 |
| 2016/0100766 A1 | 4/2016 | Yoshioka et al. | |
| 2016/0113531 A1* | 4/2016 | Visvanathan | A61B 5/02438 600/323 |
| 2016/0256117 A1* | 9/2016 | Baik | A61B 5/6803 |
| 2016/0302735 A1* | 10/2016 | Noguchi | A61B 5/02108 |
| 2017/0039702 A1 | 2/2017 | Wang et al. | |
| 2018/0042486 A1 | 2/2018 | Yoshizawa et al. | |
| 2018/0353088 A1 | 12/2018 | Nakazawa et al. | |
| 2019/0200871 A1* | 7/2019 | De Haan | A61B 5/14552 |

FOREIGN PATENT DOCUMENTS

| | | |
|---|---|---|
| JP | 2009-101088 A | 5/2009 |
| JP | 2013-208140 A | 10/2013 |
| JP | 2014-198198 A | 10/2014 |
| JP | 2016-77890 A | 5/2016 |
| JP | 2016-190022 A | 11/2016 |
| JP | 2017-93961 A | 6/2017 |

OTHER PUBLICATIONS

First Office Action issued by The State Intellectual Property Office of People's Republic of China for corresponding Chinese Patent Application No. 201880076250.X, dated Aug. 15, 2022, with an English translation.

International Search Report issued for corresponding International Patent Application No. PCT/JP2018/043004, mailed on Feb. 19, 2019, with an English translation.

Notification concerning Transmittal of International Preliminary Report on Patentability issued by the International Bureau for corresponding international application No. PCT/JP2018/043004.

Notification of Transmittal of English Translation of the International Preliminary Report on Patentability Issued by the International Bureau for corresponding international application No. PCT/JP2018/043004.

International Preliminary Report on Patentability issued by the International Bureau on behalf of the International Searching Authority under Rule 44 bis.1(a) for corresponding international application No. PCT/JP2018/043004. X English translation attached.

* cited by examiner

BIOLOGICAL INFORMATION MEASURING APPARATUS, NON-TRANSITORY COMPUTER-READABLE RECORDING MEDIUM HAVING STORED THEREIN A PROGRAM FOR CAUSING A COMPUTER TO EXECUTE A PROCESS FOR MEASURING BIOLOGICAL INFORMATION, AND METHOD FOR MEASURING BIOLOGICAL INFORMATION

CROSS-REFERENCE TO RELATED APPLICATION

This application is a continuation application of International Application PCT/JP2018/043004, filed on Nov. 21, 2018 and designated the U.S., which claims priority to Japanese Patent Application No. 2017-230362, filed on Nov. 30, 2017. The contents of these applications are incorporated herein by reference.

FIELD OF THE INVENTION

The embodiments discussed herein are related to a biological information measuring apparatus, a non-transitory computer-readable recording medium having stored therein a program for causing a computer to execute a process for measuring biological information, and a method for measuring biological information measuring that measure a fluctuation in a blood pressure of a subject.

BACKGROUND OF THE INVENTION

In recent years, various methods to obtain the physical data of subjects have been proposed in accordance with increasing healthy consciousness and increasing lifestyle-related diseases. Among them, attention has been paid to a method of using a video analysis of a skin surface of a subject as a technique for obtaining biological information through a non-contact method. This method is attracting attention because it can be accomplished using a relatively inexpensive video obtaining device such as a video camera, and also can be applied to remote medical treatment in a hospital or other facility, health management in a workplace, observation of a driver of a passenger car, and the like.

Patent Document 1 describes a biological information measuring apparatus that calculates differences in brightness information of multiple video signals obtained at different body parts of a subject at the same time, and measures a fluctuation in a blood pressure according to an increase or a decrease in the differences.

LIST OF RELATED ART DOCUMENTS

[Patent Document 1] Japanese Laid-open Patent Publication No. 2016-190022

SUMMARY OF THE INVENTION

Problem to be Solved by the Invention

In the technique described in Patent Document 1, although it is possible to measure a fluctuation in the blood pressure based on the video signal obtained by a video obtaining device, for example, it is necessary to simultaneously take video of the face and the palm of the subject. In this case, the subject has to undergo video taking with his/her face facing the camera and his/her palm also facing the camera. As described above, in the technique described in Patent Document 1, the subject have to take a posture such that two parts of the body are subjected to video taking simultaneously, which is complicated. With a foregoing problem in view, there is a demand for a technique capable of measuring a fluctuation in blood pressure even from a single part of the body.

The present invention has been made in view of the background art, and an object thereof is to provide a biological information measuring apparatus, a biological information measuring method, a non-transitory computer-readable recording medium having stored therein a program capable of easily measuring a fluctuation in a blood pressure of a subject on the basis of a video signal obtained by video taking of a predetermined part of the subject. In addition to the above object, an advantageous effect that is derived from each configuration shown in the following detailed modes to carry out the present invention and which is not obtained by the conventional technique can be regarded as another object of the present disclosure.

Means for Solving the Problems

The present invention provides the following various embodiments.

[1] A biological information measuring apparatus includes: a distortion calculating unit that calculates, based on video pulse wave information representing a video pulse wave expressing a temporal change in a brightness value included in a video signal of a predetermined part of a subject, a waveform distortion obtained from a heartbeat basic component containing a frequency component of a heartbeat frequency band corresponding to a heart rate of the subject and a heartbeat high-frequency component related to a waveform of a pulse wave and containing a frequency component of a frequency band higher than the heartbeat frequency band, the heartbeat basic component and the heartbeat high-frequency component being included in the video pulse wave; and a measuring unit that measures a fluctuation in a blood pressure of the subject based on the waveform distortion calculated by the distortion calculating unit.

[2] The biological information measuring apparatus according to [1], wherein: the measuring unit measures an increase of the waveform distortion as a decline of the blood pressure and a decrease of the waveform distortion as a rise of the blood pressure.

[3] The biological information measuring apparatus according to [1], wherein: the wave distortion is expressed by a difference in a time domain between the heartbeat basic component and the heartbeat high-frequency component; and the distortion calculating unit includes a feature point detecting unit that detects, from the video pulse wave information, a feature point of a basic wave formed of a frequency component of the heartbeat frequency band; and a vertex detecting unit that detects, from the video pulse wave information, a vertex of an end diastolic segment of the video pulse wave.

[4] The biological information measuring apparatus according to [1], wherein: the waveform distortion is expressed by a ratio between the heartbeat basic component and the heartbeat high frequency-component in frequency domain; and the distortion calculating unit includes a converting unit that obtains a sum of Fourier coefficients of Fourier series of each of the heartbeat basic component and the heartbeat high-frequency component, and a ratio calculating unit that calculates ratio, as the ratio in the frequency domain, of the sum of the Fourier coefficients of the heartbeat high-frequency component to the sum of the Fourier coefficients of the Fourier series of the heartbeat basic component.

[5] The biological information measuring apparatus according to [1], wherein: the measuring unit measures a blood pressure value corresponding to the waveform distortion calculated by the distortion calculating unit based on association information representing the waveform distortion of the subject and a blood pressure value of the subject.

[6] The biological information measuring apparatus according to [1], wherein: the measuring unit calculates a blood pressure value by multiple regression analysis using a multiple regression equation using the blood pressure value of the subject as an objective variable and the waveform distortion, the heart rate, and a pulse wave amplitude of the subject as explanatory variables.

[7] The biological information measuring apparatus according to [1], wherein: the video pulse wave information includes a temporal change in a brightness value included in a video signal of a part where a peripheral arteriole increases a peripheral vascular resistance by being innervated by a sympathetic nerve when blood pressure rises.

[8] The biological information measuring apparatus according to [1], wherein: the video pulse wave information includes a temporal change in a brightness value included in a video signal of a palm of the subject.

[9] A non-transitory computer-readable recording medium having stored therein a program for causing a computer to execute a process for measuring biological information, the process comprising: a distortion calculating unit that calculates, based on video pulse wave information representing a video pulse wave expressing a temporal change in a brightness value included in a video signal of a predetermined part of a subject, a waveform distortion obtained from a heartbeat basic component containing a frequency component of a heartbeat frequency band corresponding to a heart rate of the subject and a heartbeat high-frequency component related to a waveform of a pulse wave and having a frequency component of a frequency band higher than the heartbeat frequency band, the heartbeat basic component and the heartbeat high-frequency component being included in the video pulse wave; and a measuring unit that measures a fluctuation in a blood pressure of the subject based on the waveform distortion calculated by the distortion calculating unit.

[10] A method for measuring biological information, the method comprising: a distortion calculating step that calculates, based on video pulse wave information representing a video pulse wave expressing a temporal change in a brightness value included in a video signal of a predetermined part of a subject, a waveform distortion obtained from a heartbeat basic component containing a frequency component of a heartbeat frequency band corresponding to a heart rate of the subject and a heartbeat high-frequency component related to a waveform of a pulse wave and having a frequency component of a frequency band higher than the heartbeat frequency band, the heartbeat basic component and the heartbeat high-frequency component being included in the video pulse wave; and a measuring step that measures a fluctuation in a blood pressure of the subject based on the waveform distortion calculated by the distortion calculating step.

Effect of the Invention

The present invention can easily measure a fluctuation in a blood pressure of a subject by calculating a waveform distortion from the video signal obtained from one part of the body of the subject.

EMBODIMENT TO CARRY OUT THE INVENTION

Figure 1:
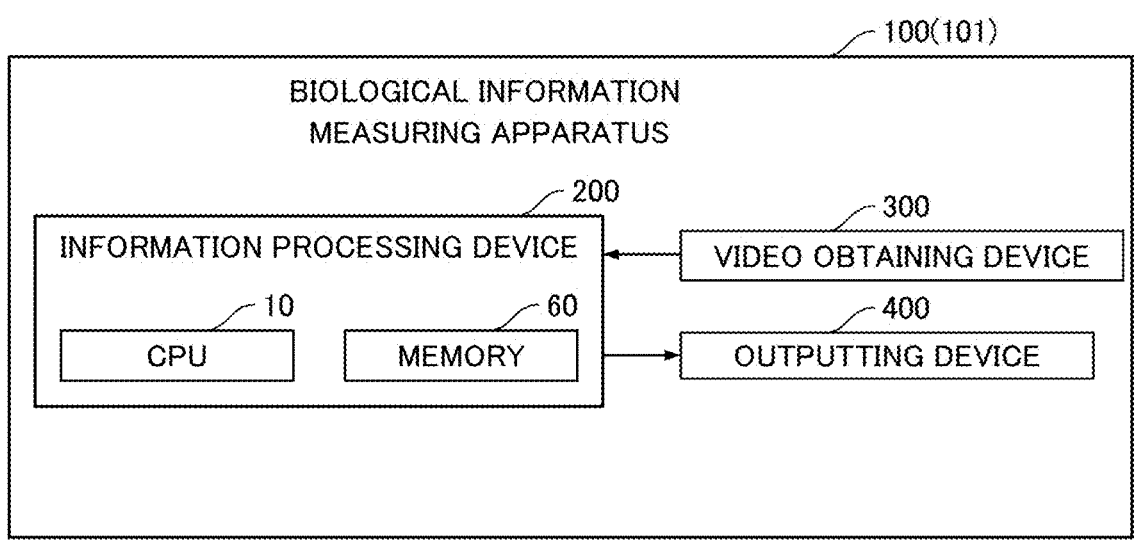
FIG. 1 is a block diagram illustrating an example of the hardware configuration of a biological information measuring apparatus according to a first embodiment.

Hereinafter, a biological information measuring apparatus according to embodiments of the present invention will be described with reference to the accompanying drawings. The following embodiments are merely illustrative and are not intended to exclude the application of various modifications and techniques not explicitly described in the embodiments. Each configuration of the present embodiments can be variously modified and implemented without departing from the scope thereof. Also, the configuration can be selected or omitted according to the requirement or appropriately combined. In the drawings, same reference numbers designates the same or similar parts, unless otherwise specified.

Throughout this specification, numerical values or physical property values being expressed by being interposed by "-" is used as a range including numerical values or physical property values of the upper and the lower limits. For example, the expression of a range of "1-100" includes both the lower limit value "1" and the upper limit value "100", and represents "1 or more and 100 or less". The same is applied to notation for other numeric ranges.

1. First Embodiment

A biological information measuring apparatus according to the first embodiment will be described with reference to FIGS. 1-10. Hereinafter, in the description of the first embodiment, this first embodiment is also simply referred to as the present embodiment. The biological information measuring apparatus according to the present embodiment calculates a waveform distortion of the heartbeat basic component and the heartbeat high-frequency component included in a video pulse wave (VPG; video plethysmogram) based on the video pulse wave information of the predetermined part of the subject. Furthermore, in the present embodiment, the waveform distortion is calculated as a difference between the heartbeat basic component and the heartbeat high-frequency component in the time domain. Then, the biological information measuring device according to the present embodiment measures (estimates) a fluctuation in a blood pressure from the calculated difference in the time domain.

[1-1. Configuration]
[1-1-1. Hardware Configuration]

As shown in FIG. 1, the biological information measuring apparatus 100 according to the present embodiment includes at least an information processing device 200. The biological information measuring apparatus 100 further includes a video obtaining device 300 and an outputting device 400. The biological information measuring apparatus 100 further includes an input device (not shown) such as a keyboard and a mouse. The information processing device 200 is configured as, for example, a computer for processing measurement data obtained by the video obtaining device 300. The information processing device 200 includes a central processing unit (CPU) 10 and a memory 60, which are communicably connected to each other via a buses (not illustrated). The information processing device 200 may be an information device such as a PC (Personal Computer), a smart phone, or a tablet terminal. The information processing device 200 measures a fluctuation in a blood pressure by analyzing a video signals of a subject.

In this embodiment, a computer is a concept including hardware and an operating system and means hardware that operates under control of the operating system. If the application program solely operates the hardware, not requiring an operating system, the hardware itself is equivalent to computer. The hardware includes at least a microprocessor, such as a CPU, and a means for reading a computer program recorded in a recording medium.

Hereinafter, the configuration of each component will be described.

<CPU>

Figure 2:
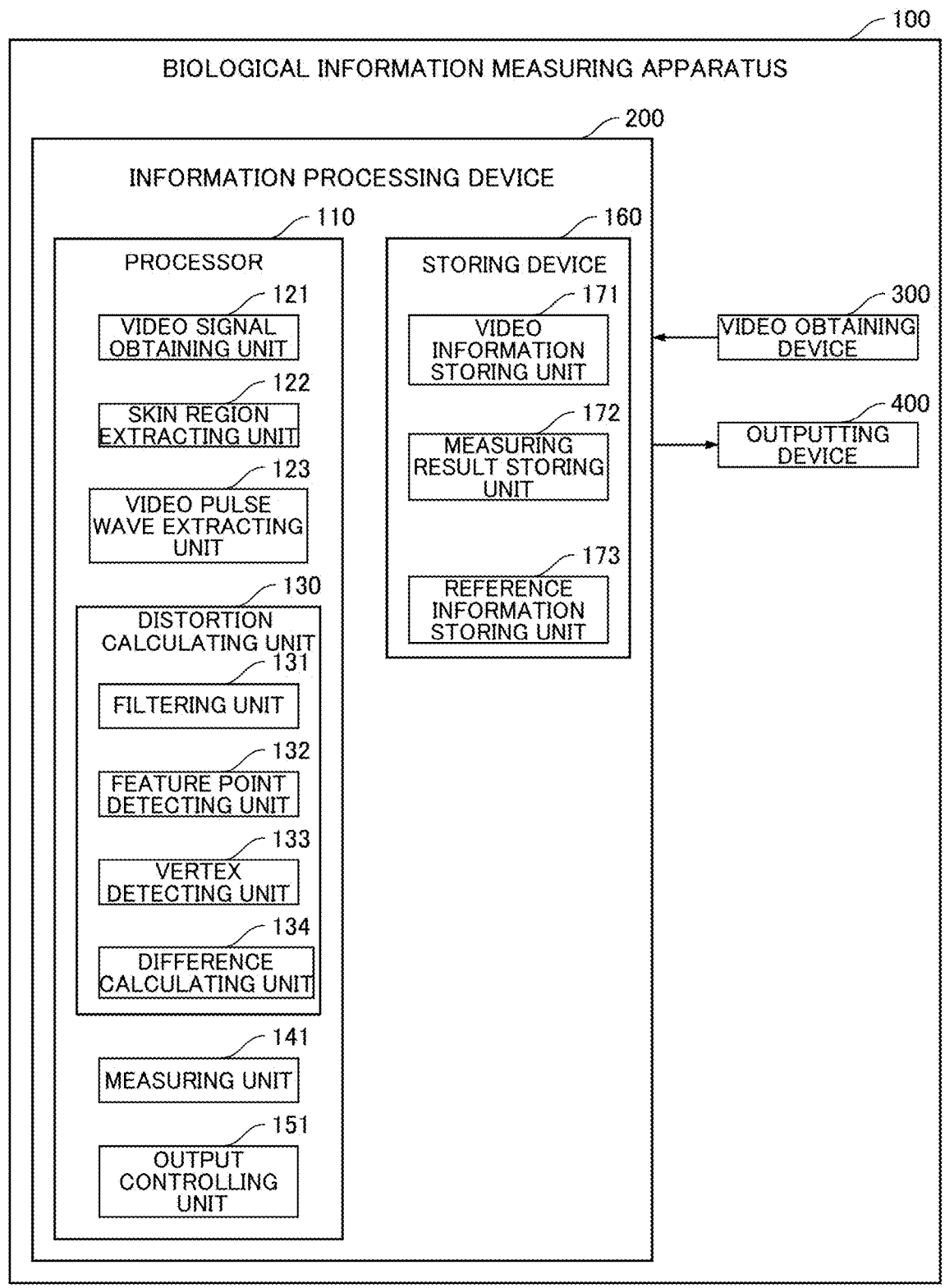
FIG. 2 is a block diagram illustrating an example of the functional configuration of a biological information measuring apparatus according to a first embodiment.

The CPU 10 is a processing device that performs various controls and operations and achieves various functions by reading and executing a program of the present embodiment stored in memory 60 and to be described below. The CPU 10 functions as the respective functional units of a processor 110, as illustrated in FIG. 2, by executing this program. It should be noted that the means for achieving the processing function in the processor 110 is not limited to a program, and may alternatively be a hardware installed in the information processing apparatus 200. For example, the processor 110 may be configured as a one-chip microcomputer including a ROM, a RAM, a CPU, and the like, or may be configured as an electronic circuit such as a DSP (Digital Signal Processor), an FPGA (Field-Programmable Gate Array), an ASIC (Application Specific Integrated Circuit), and the like.

<Memory>

The memory 60 is a data storing device that stores various data and programs. In this embodiment, the memory 60 functions as a data storing device, which alternatively may be a volatile memory, such as a RAM (Random Access Memory), a non-volatile memory such as ROM, flash memory, a HDD (Hard Disk Drive), an SSD (Solid State Device), and an optical disk.

<Video Obtaining Device>

The video obtaining device 300 is an video camera having a image sensor using a CCD (Charge Coupled Device) or a CMOS (Complementary Metal Oxide Semiconductor) as an imaging device. Three or more light receiving elements such as R (red), G (green), and B (blue) can be mounted on the video obtaining device 300. Further, the video obtaining device 300 may be a reflective photosensor equipped with a green LED. The video obtaining device 300 takes a video of a predetermined part of the body of the subject, and obtains a video signal of the predetermined part. Then, the video obtaining device 300 outputs a video signal to the video signal obtaining unit 121 to be described below (see FIG. 2).

The predetermined part to be the part which being subjected to video taking of the body of the subject by the video obtaining device 300 is not particularly limited, but is preferably a part of the skin surface whose video can be easily taken usually because of being largely exposed and being exemplified by a hand and a face. Above all, the palm, the forehead, and the cheeks are preferably used in view of the size of the video taking part. In particular, from the viewpoint of easiness in obtaining a video pulse wave having a high signal-to-noise ratio of a signal, a part in which the arteriole rises the peripheral vascular resistance under control of the sympathetic nerve when the blood pressure rises is preferable. Such a part may be a peripheral region such as a limb of a hand, a leg, or the like, and among these, a hand is preferable, and a palm of a hand is more preferable. The video included in the video signal obtained by the video obtaining device 300 may be a video including only a part of the body of the subject described above, a video including two or more parts of the body of the subject, or a video including only a region of a part of the body of the subject.

<Outputting Device>

An example of the outputting device 400 is a display such as a CRT (Cathode Ray Tube), an LCD (Liquid Crystal Display), or an organic electroluminescence display (Organic Light-Emitting Diode Display). The outputting device 400 can display information processed by a processor 110, information to be stored in the storing unit 160, and the like. For example, the outputting device 400 can display the video of a video signal obtained by a video signal obtaining unit 121. The outputting device 400 can display the skin region extracted by a skin region extracting unit 122. Further, the outputting device 400 can display the waveform distortion calculated by a distortion calculating unit 130. In addition, the outputting device 400 can display a fluctuation in a blood pressure of a subject measured by the measuring unit 141. The outputting device 400 may also display a GUI (Graphical User Interface) for receiving input operations from an inputting device. As the outputting device 400, a sound outputting device such as a speaker may be used.

[1-1-2. Functional Configuration]

As shown in FIG. 2, being functionally exhibited, the biological information measuring apparatus 100 includes the information processing device 200, the video obtaining device 300, and the output device 400. Further, being functionally represented, the information processing device 200 includes the processor 110 and a storing unit 160.

Hereinafter, the configuration of each elements will be now described.

<Storing Unit>

The storing unit 160 uses a memory 60 to store data by a file system or a database system. The storing unit 160 of the present embodiment includes a video information storing unit 171, a measuring result storing unit 172, and a reference information storing unit 173. For example, the storing unit 160 can store data such as a video signal, a measuring result, and reference information, which will be described below. Further, the storing unit 160 previously stores programs to achieve, when being executed by CPU10, the functions as the video signal obtaining unit 121, the skin region extracting unit 122, a video pulse wave extracting unit 123, the distortion calculating unit 130, the measuring unit 141, and an output controlling unit 151 of the processor 110 to be described below. These programs will be collectively referred to as the program of the present embodiment (also referred to as biological information measuring program). The elements of the storing unit 160 will be described below. The biological information measuring program is configured as a program that is executed by CPU10 to function as at least the distortion calculation unit 130 and the measuring unit 141.

<Processor>

The processor 110 is a functional unit that is subjected to arithmetic process performed by the CPU 10, and each function is configured as an individual program. As shown in FIG. 2, the processor 110 functions as the video signal obtaining unit 121, the skin region extracting unit 122, the video pulse wave extracting unit 123, the distortion calculating unit 130, the measuring unit 141, and the output controlling unit 151. The description of each elements of the processor 110 will be described below.

The program of the preset embodiment is provided in a form of being recorded in a computer-readable recording medium, such as a flexible disk, a CD (e.g. CD-ROM, CD-R, CD-RW), a DVD (e.g., DVD-ROM, DVD-RAM, DVD-R, DVD+R, DVD-RW, DVD+RW, HD DVD), a Blu-ray disk, a magnetic disk, an optical disk, a magneto-optical disk, a USB memory, and an SD memory card. The information processing device 200 then reads a program from the recording medium and transmits and stores the read program to and into an internal storing device (e.g., the memory 60) or an external storing device for future use. Alternatively, the program may be recorded in a storing device (recording medium) (not shown) such as a magnetic disk, an optical disk, or a magneto-optical disk, and provided from such a storing device to the information processing apparatus 200 via a network.

[1-1-3. Storing Unit]

<Video Information Storing Unit>

The video information storing unit 171 stores video signals. Specifically, the video information storing unit 171 stores video signals of a subject obtained by the video obtaining unit 300. For example, the video information storing unit 171 stores video signals indicating a video including a predetermined part of the subject. The video information storing unit 171 stores a video signal and the temporal information of the time of taking a video of the subject in association with each other.

<Measuring Result Storing Unit>

The measuring result storing unit 172 stores a measuring result of a measuring process executed by the processor 110 to be described below. Specifically, the measuring result storing unit 172 stores, for example, waveform distortion calculated by the distortion calculating unit 130, information about a fluctuation in a blood pressure measured by the measuring unit 141.

At this time, the measuring result storing unit 172 stores the measuring information that associates the date and time of the measurement with the measuring result for each subject. Here, the date and time of measurement indicates a date and a time at which a video of a predetermined part of the subject is taken and a fluctuation in blood pressure is measured based on the taken video signal. In addition, the measuring result indicates the result of an item measured at each date and time of measurement.

<Reference Information Storing Unit>

The reference information storing unit 173 stores reference information referred to in a measuring process performed by the processor 110, which will be described below. Specifically, the reference information storing unit 173 stores reference information that is referred to when the measuring unit 141 measures information related to a fluctuation in a blood pressure of a subject. The reference information indicates information to be referred to when the measuring unit 141 measures a fluctuation in a blood pressure. The measuring result of a fluctuation in the blood pressure measured by the measuring unit 141 is based on the waveform distortion. For the above, the reference information storing unit 173 stores such reference information for deriving the absolute value of the blood pressure from the waveform distortion, so that the measuring unit 141 can derive the blood pressure value from the waveform distortion using the reference information. Examples of the reference information include association information, conversion information, and the like. The reference information may be stored for each subject, or may be stored, being categorized according to age and gender of the subject. In addition, multiple pieces of association information may be stored for each of various environments such as a measurement point and a measurement time. Furthermore, the association information may be periodically updated.

The association information is information for estimating (deriving) the absolute value of a blood pressure from a waveform distortion based on the association between a waveform distortion and a blood pressure value. A video signal is obtained by using the biological information measuring apparatus 100 to calculate the waveform distortion, and also a blood pressure value at the time a video signal is obtained is measured using the sphygmomanometer in advance. Then the waveform distortion and the blood pressure are stored in the reference information storing unit 173 in association with each other.

The conversion information is information for converting a waveform distortion into the absolute value of the blood pressure, and is exemplified by a conversion coefficient. A video signal is obtained by using the biological information measuring apparatus 100 to calculate the waveform distortion, and also a blood pressure value at the time a video signal is obtained is measured in advance using the sphygmomanometer. Further, the conversion information is calculated by performing calibration based on the association between the waveform distortion and the blood pressure value. The conversion information is stored in the referenced information storing device 173.

The reference information includes data such as a regression coefficient, and a determination coefficient, which are used in a multiple regression analysis using a multiple regression equation, which will be described below. A video signal is obtained by using the biological information measuring apparatus 100, to calculate a wave distortion, and also a blood pressure value, a heart rate, and a pulse wave amplitude when the video signal is obtained are measured in advance with a sphygmomanometer, a heart rate meter, an electrocardiograph, respectively. In addition, the regression coefficients and the determination coefficients of the multiple regression equations are calculated using these data. The regression coefficients and the determination coefficients are then stored in the reference information storing unit 173.

[1-1-4. Processor]

<Estimating of Fluctuation in Blood Pressure>

The processor 110 calculates a waveform distortion a video signal of a predetermined part of a subject, and estimates a fluctuation in the blood pressure from the fluctuation in the calculated waveform distortion. Here, the principle of the estimating of a fluctuation in the blood pressure using the waveform distortion will now be described.

A waveform distortion represents a distortion between a heartbeat basic component including a frequency component of a heartbeat frequency band corresponding to a heart rate of the subject and a heartbeat high-frequency component including a frequency component of a frequency band related to a shape of a pulse wave waveform and higher than the heartbeat frequency band. The video pulse wave includes a heartbeat basic component derived from a heartbeat, and further includes, being affected by a fluctuation in the blood pressure, a heartbeat high-frequency component. A waveform distortion indicates a change in a waveform composed of a heartbeat basic component due to a fluctuation in the blood pressure. A waveform distortion can be expressed by a change in a time domain or by a change in a frequency domain. In particular, a waveform distortion may be expressed by a difference between the heartbeat basic component and the heartbeat high-frequency component in the time domain, or may also be expressed by a ratio in the frequency domain of the heartbeat basic component and the heartbeat high-frequency component. In the present embodiment, description will now be made in relation to a case where a waveform distortion is expressed by the difference in the time domain between the heartbeat basic component and the heartbeat high-frequency component.

The heartbeat basic component includes at least a frequency component of the heartbeat frequency band, and may include the frequency component of the heartbeat frequency band and the frequency component of the frequency band lower than the heartbeat frequency band, but is preferably composed of the frequency component of the heartbeat frequency band. The heartbeat high-frequency component includes a frequency component in a frequency band higher than the heartbeat frequency band, and may be composed of a frequency component in a frequency band higher than the heartbeat frequency band. Alternatively, the heartbeat high-frequency component may include a frequency component of a frequency band higher than the heartbeat frequency band and a frequency component of the heartbeat frequency band. The heartbeat high-frequency component may include a frequency component of a frequency band higher than the heartbeat frequency band, a frequency component of the heartbeat frequency band, and a frequency component of a frequency band lower than the heartbeat frequency band.

Figure 3:
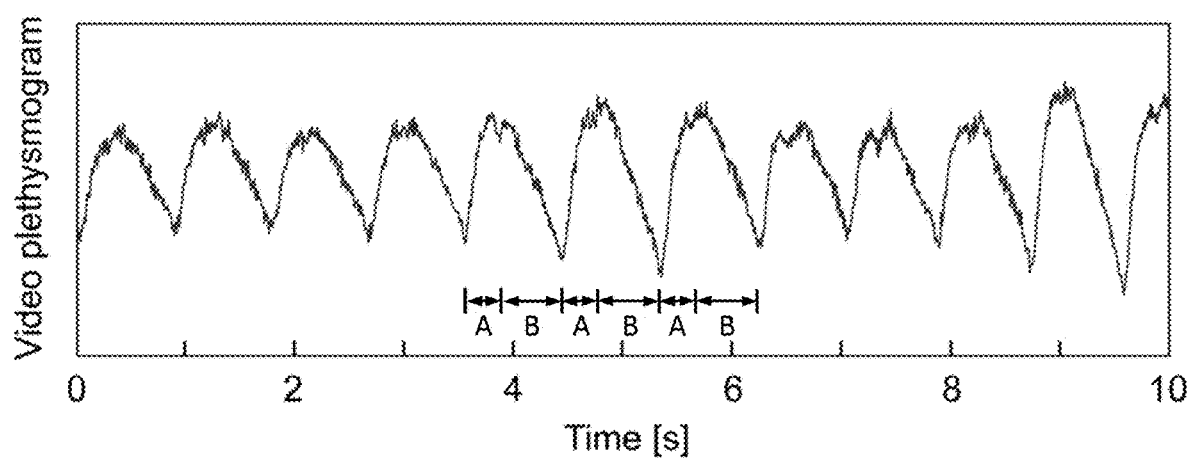
FIG. 3 is a graph illustrating an example of a video pulse wave.

FIG. 3 shows a video pulse wave of a subject. As shown in FIG. 3, the video pulse wave is observed as a sinusoidal waveform exhibiting a periodic increase and decrease of the systole A and the diastole B in synchronization with the cardiac cycle of the heartbeat. The video pulse wave is observed as a waveform including a low-frequency component and a high-frequency component in addition to a component corresponding to the heartbeat. In FIG. 3, the horizontal axis represents the time (seconds) (Time[s]), and the vertical axis represents the intensity of a video pulse wave (Video plethysmogram). Thereafter, the same is applied to FIGS. 4(*a*) and 4(*b*).

The heartbeat basic component can be obtained by applying the band-pass filtering process for passing a frequency component of the heartbeat frequency band to the video pulse wave. At this time, the video pulse wave before the bandpass filtering process is applied is regarded as a heartbeat high-frequency component. In contrast to the above, the heartbeat basic component to which the band-pass filtering process is applied is a sinusoidal periodic waveform composed of a frequency component of the heartbeat frequency band, and is a basic wave of the video pulse wave. In the basic wave, a pulse wave occurring in response to one beat of the heart appears as one peak of a waveform after a filtering process.

Figure 4:
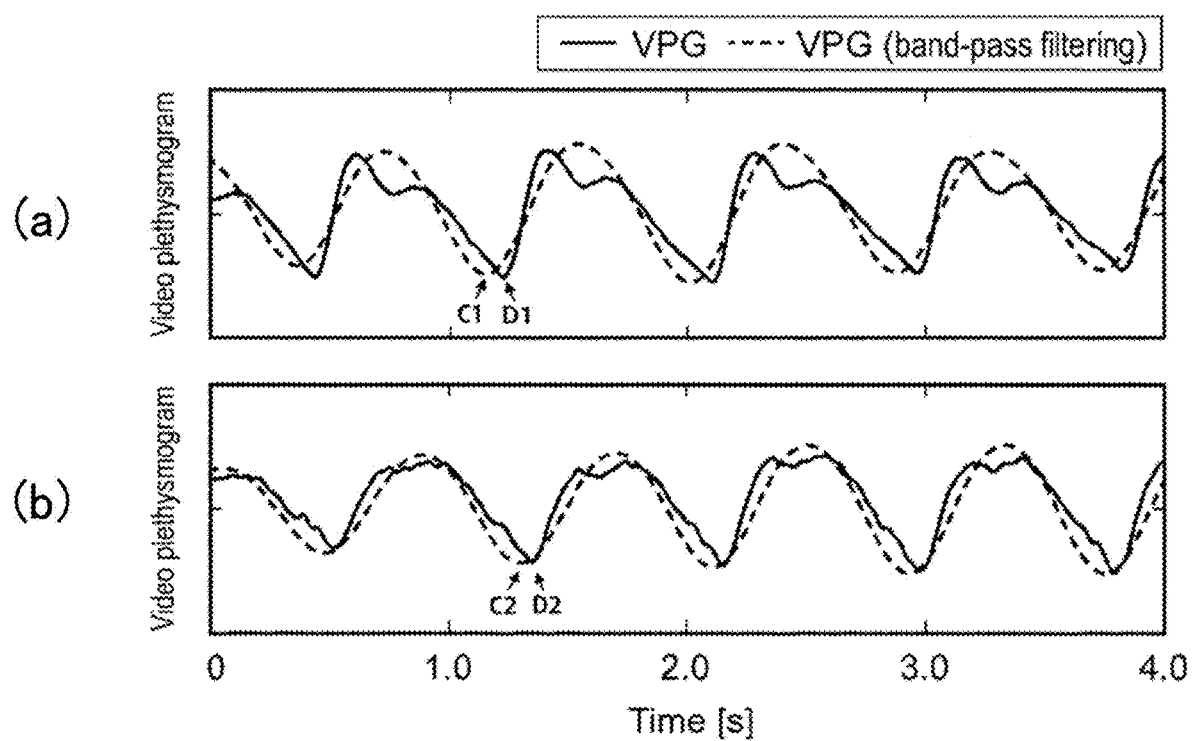
FIG. 4 is graphs illustrating a waveform before a filtering process of a video pulse wave and a waveform after the filtering process, (a) illustrating a video pulse wave in a low blood pressure state, (b) illustrating a video pulse wave in a high blood pressure state.

Here, in FIGS. 4(*a*) and (*b*), the video pulse wave, which is the heartbeat high-frequency component before the filtering process, is indicated by a solid line (VPG). The basic wave, which is a heartbeat basic component obtained from the video pulse wave by completing the band-pass filtering process, is indicated by a broken line (VPG (band-pass filtering)). Note that FIG. 4(*a*) and FIG. 4(*b*) are a video pulse wave and a basic wave obtained from the same part of the same subject, and FIG. 4(*a*) shows a waveform in a state in which the blood pressure is lower than FIG. 4(*b*). As shown in FIG. 4(*a*) and FIG. 4(*b*), the basic wave shows a sinusoidal waveform. The local minimum points C1 and C2 of the basic wave appear on the left side of the vertexes D1 and D2 of the end diastolic segment of the video pulse wave, that is, at earlier times. Furthermore, as compared with the time interval between the local minimum point C1 of the basic wave and the vertex D1 of the end diastolic segment of the video pulse wave in the state of a low blood pressure of FIG. 4(a), the time interval between the local minimum point C2 of the basic wave and the vertex D2 of the end diastolic segment of the video pulse wave in the state of a high blood pressure of FIG. 4(b) is narrower.

Conventionally, from the relationship between an ECG (electrocardiogram) and a PPG (photoplethysmograph), a PTT (Pulse Transit Time; pulse wave propagation time) indicating the time difference to the vertex of the end diastolic segment of the waveform of the photoplethysmograph is calculated on the basis of the R wave of the electrocardiogram. A pulse transit time is defined as the time during which a pulse wave travels through a blood vessel and is known to correlate with a fluctuation in a blood pressure. The present inventors have found that the time difference from a feature point of the basic wave to the vertex of the waveform of the video pulse wave has a correlation with a fluctuation in a blood pressure by using the basic wave representing the frequency component of the heartbeat frequency band and using this basic wave as a reference such as the R wave of the electrocardiogram.

The feature point of the basic wave is not particularly limited, but may be, for example, a local minimum point, a local maximum point, a maximum point of differentiation of the basic wave. Further, a vertex of the video pulse wave is not particularly limited, and may be for example, a point where the value of the video pulse wave indicating the plethysmogramis the smallest, a point where the value of the video pulse wave is the largest, a point where the velocity pulse wave serving as the first-order differentiated waveform of the video pulse wave is the largest, a point where the acceleration pulse wave serving as the second-order differentiated waveform of the video pulse is the largest. In the present embodiment, a case where a local minimum point is used as a feature point of the basic wave will be described as an example. In the present embodiment, a case where a point at which the value of the video pulse wave is the smallest is used as the vertex of the video pulse wave will be described as an example. More specifically, a point (end diastole point) that is the smallest at the end diastole segment of the video pulse wave will be described as an example.

The estimating of a fluctuation in the blood pressure using the waveform distortion will be further detailed with reference to FIGS. 5(a) and 5(b). FIG. 5(a) is a model of a blood circulation system simulating an electric circuit using a three-element windkessel model. In FIG. 5(a), the term v(t) represents a pressure from the heart, i.e., the blood pressure. The symbol C represents the volume of the blood vessel. The terms $R_a$ and $R_c$ represent the resistances of the arterial and capillary vessels, respectively. Furthermore, the change in the video pulse wave is simulated by q(t), which is the amount of charge in the capacitor. Incidentally, the symbol "t" represents a time, v (t) and q (t) are time functions. The transient change in q(t) is represented by the following equation (1).

$$q(t) = \frac{CR_c}{R_a + R_c} v(t) \left\{ 1 - e^{-\frac{1}{C}\left(\frac{1}{R_a} + \frac{1}{R_c}\right)t} \right\} \quad (1)$$

Figure 5:
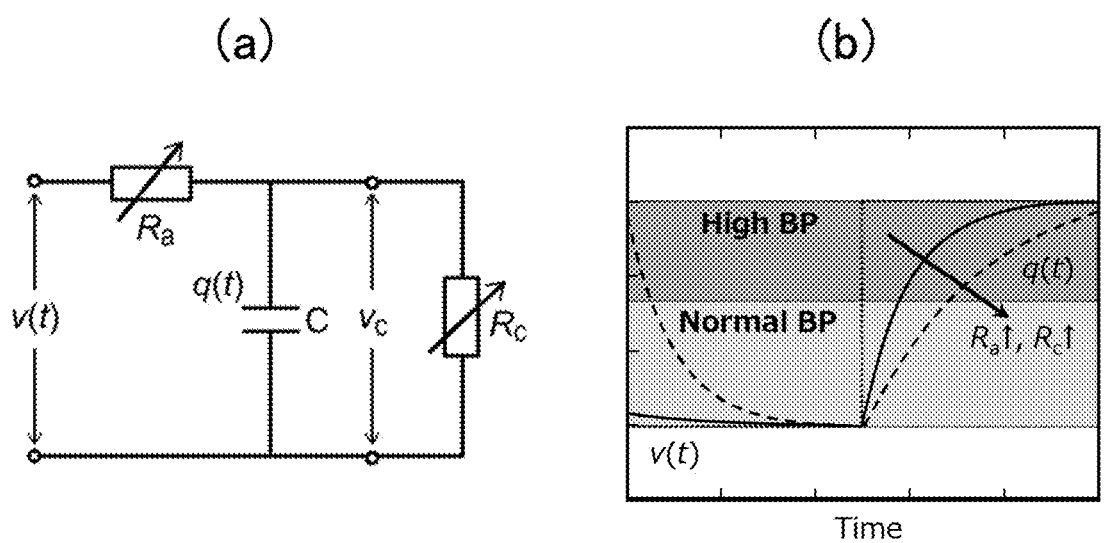
FIG. 5 is a diagram illustrating a blood circulation system, (a) being a model diagram in which the circulation system is simulated by an electric circuit, and (b) being a graph illustrating changes in blood pressure and in waveform of a video pulse wave in the model.

FIG. 5(b) shows the change in q(t) with respect to v(t) in the circuit shown in FIG. 5(a) by expressing the time (seconds) (Time[s]) on the horizontal axis, the magnitude of q(t) on the vertical axis as a solid line and a broken line, and the change in v(t) as a dotted line. At this time, v(t) simulates a pulse wave from the heart. In other words, FIG. 5 (b) represents a change in the waveform of the video pulse wave with respect to the bias of the pulsation.

Specifically, as shown in FIG. 5(b), the region (High BP) where v(t) is higher has a the rate of increase (slope) of q(t) is gentler than that of the region (Normal BP) where v(t) is normal. Further, when the blood pressure increases, the time constants of the circuits shown in FIG. 5(a) are increased by increasing of the resistances ($R_a$, $R_c$) of the blood vessel. As a result, as compared with a curve represented by a broken line of q(t) having a low resistance value, the curve represented by a solid line of q(t) having a high resistance value has a gentler increase rate. From the change in q(t) with respect to v(t) in the above-described model, it is estimated that the waveform of the video pulse wave changes with the change in the blood pressure.

Figure 6:
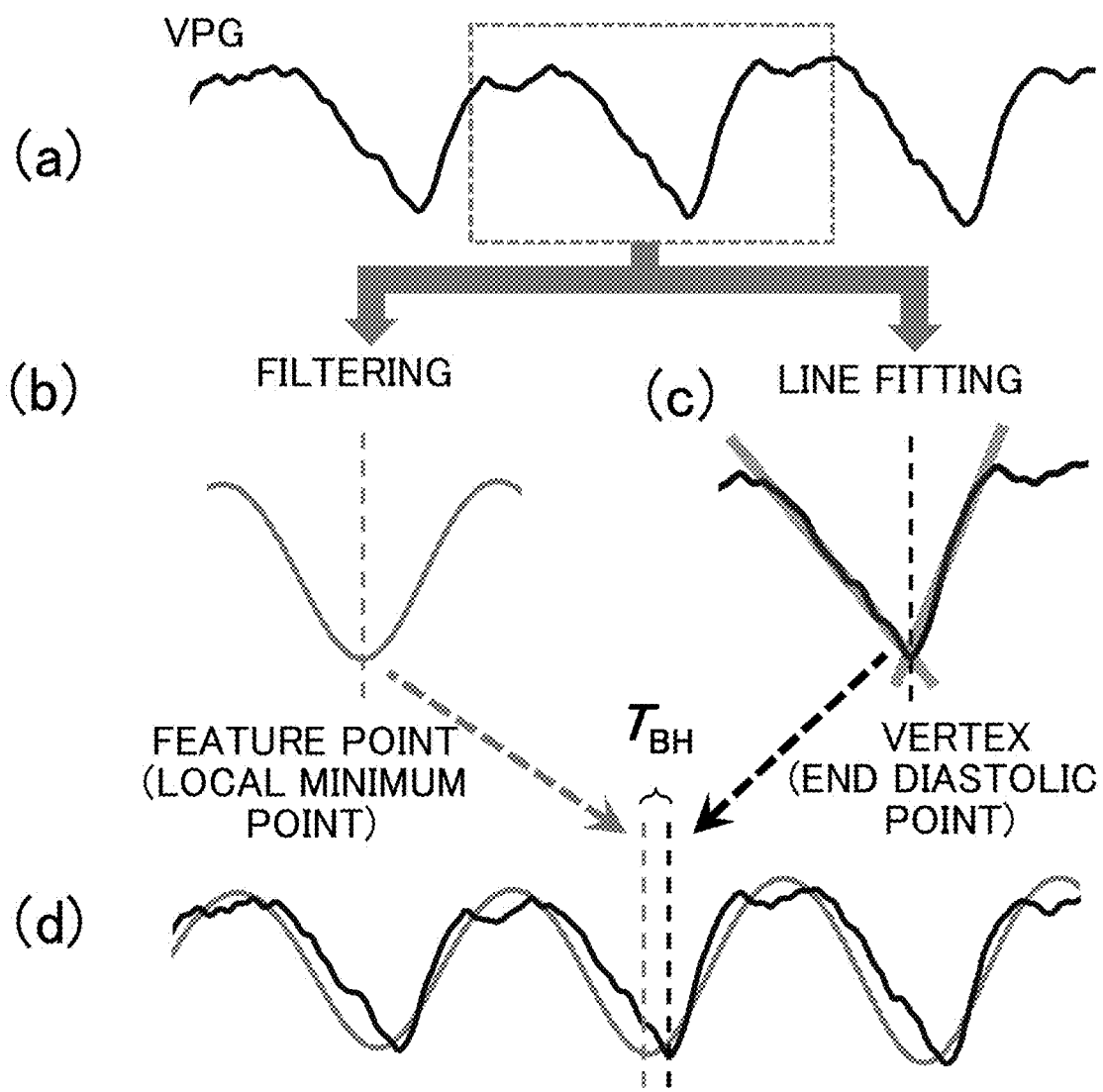
FIG. 6 is a diagram illustrating a difference in the time domain, (a) representing a video pulse wave, (b) representing a basic wave and a feature point (local minimum point), (c) representing a video pulse wave and a vertex (end diastolic point), and (d) representing a difference $T_{BH}$ in the time domain.

Further, referring to FIGS. 6(a) to 6 (d), a difference $T_{BH}$ in the time domain to be used for estimating of a fluctuation in a blood pressure from a video pulse wave will be described for estimating a fluctuation in a blood pressure using a wave distortion.

The frequency component of the above-mentioned basic wave included in the video pulse wave is usually 0.7-1.8 Hz corresponding to a normal heart rate of 40-110 bpm. For one cycle of the video pulse wave of FIG. 6(a), FIG. 6(b) shows the basic wave to which the band-pass filtering processing is applied, and FIG. 6(c) shows the non-processed original video pulse wave. In this case, FIG. 6(b) shows a basic wave having undergone the band-pass filtering process (Bandpass filtering) using a bandpass filter having a passband of 0.7-1.8 Hz. Then, as shown in FIG. 6(b), a local minimum point, which is a feature point, is detected from the basic wave.

On the other hand, in FIG. 6(c), the end diastolic point is detected from the original video pulse wave. The end diastolic point is the vertex of the end diastolic segment of the video pulse wave. The method of detecting the vertex is not particularly limited, and a known method used for detecting the end point of a curve can be used. First of all, long-period vibrations such as respiration and high-frequency noise are removed from the original video pulse wave in the present embodiment. Further, the vertex at the end diastolic point is detected by fitting a straight line (line fitting) to each of the trajectories on the ascending side (systolic side) and the descending side (diastolic side) of the video pulse wave excluding the long-period vibration and obtaining the intersection of the two straight lines.

As shown in FIG. 6(d), the difference $T_{BH}$ in the time domain is calculated as the time difference between the feature point and the vertex. FIG. 6(d) illustrates a waveform obtained by superimposing the basic wave of FIG. 6(b) and the video pulse wave of FIG. 6(c). FIGS. 6(a)-6(d) exemplarily illustrate only the difference $T_{BH}$ in the time domain of one cycle. Similarly, the difference $T_{BH}$ in time domain can be calculated from the feature point and a vertex corresponding to each heartbeat.

Here, when the blood pressure fluctuates, the inclination of the straight line fitted to the systolic side usually fluctuates. On the other hand, normally, the inclination of the straight line fitted to the diastolic side does not easily fluctuate. As described with reference to the models of FIGS. 5(a) and 5(b), when the blood pressure rises and the resistance $R_c$ corresponding to the peripheral vascular resistance rises, the change in the video pulse wave becomes gentle. At this time, the inclination of the straight line fitted to the systolic side becomes small (gentle). Then, shifting of vertices to the left, i.e., earlier time, decrease the differential $T_{BH}$ in the time domain. On the other hand, when the blood pressure declines and the resistance $R_c$ decreases, the change in the video pulse wave becomes steep. At this time, the slope of the straight line fitted to the systolic side becomes large (steep). Then, the shifting of vertices to the right, i.e., later time, increases the differential $T_{BH}$ in the time domain.

As described above, by utilizing the distortion of the waveforms with respect to the basic wave, which occurs at the end diastole of the video pulse wave, it is possible to measure the change in the difference $T_{BH}$ in the time domain, which shows a negative correlation with the increase and decrease of the blood pressure. In other words, as described with reference to FIGS. 4(a) and 4(b), a fluctuation in a blood pressure can be measured on the basis of the difference $T_{BH}$ in the time domain corresponding to the time domain between the heartbeat basic component and the heartbeat high-frequency component.

The biological information measuring device 100 according to the present embodiment measures a fluctuation in a blood pressure by measuring a fluctuation in the difference $T_{BH}$ in the time domain from the video pulse wave, which represents a temporal fluctuation in the brightness value of the video signal on the basis of the principles described above. Hereinafter, in relation to the process by the biological information measuring apparatus 100, the process of extracting a pulse wave information from a video signal and the process of calculating a difference $T_{BH}$ in the time domain from the extracted pulse wave information will be subsequently described with reference to the respective elements.

<Video Signal Obtaining Unit>

The video signal obtaining unit 121 obtains a video signal indicating a video of a predetermined part of the body of the subject via the video obtaining unit 300. The video signal obtaining unit 121 outputs the obtained video signal of the subject to the skin region extracting unit 122. The video signal obtaining unit 121 may obtain a video signal by reading the video signal stored in the video information storing unit 171. The video signal obtaining unit 121 may obtain a video signal by receiving data containing a video signal which signal is stored in an external communication terminal or an external storing device via a network, an electric line, or the like.

<Skin Region Extracting Unit>

The skin region extracting unit 122 extracts a skin region of the subject included in a video of a video signal obtained by the video obtaining device 300. Specifically, the skin region extracting unit 122 automatically extracts the skin region based on the color information in the video. Alternatively, the skin region extracting unit 122 extracts a region designated by the operator via an input unit (not shown) as a skin region. The skin region extracting unit 122 transmits the coordinates of the extracted skin region to the video pulse wave extracting unit 123. The target to be processed by the skin area extracting unit 122 may be a real-time video obtained by the video obtaining device 300 or a previous video stored by the video data storing device 171.

In cases of automatically extracting a skin region based on the color information in the video, the skin region extracting unit 122 can extract the skin region of the subject by extracting a region exhibiting the skin color from the video. Specifically, the skin region extracting unit 122 extracts all coordinates (coordinates of pixels) indicating a color (brightness value) corresponding to the skin color in the two-dimensional coordinates of the video, and extracts a region in which pixels of consecutive coordinates in the extracted coordinates are grouped as a skin region. In this manner, the skin region extracting unit 122 can extract a skin region corresponding to a predetermined part of the body of the subject by extracting a region in which pixels having consecutive coordinates are grouped. At this time, the skin region extracting unit 122 may extract a region corresponding to a specific part as a skin region by performing image determination and recognizing the specific part of the body of the subject. The color (brightness value) corresponding to the skin color can be arbitrarily set. For example, a brightness value in a predetermined range may be set for each race, and coordinates indicating the brightness value within the set range in the video may be extracted as coordinates of the skin color.

When a region assigned by an operator is set as a skin region, a desired region in a video can be set as a region of interest (ROI) by operating an input unit such as a mouse or a touch panel. After the region of interest is set, the skin region extracting unit 122 extracts the set region as a skin region.

The skin region extracting unit 122 executes the above skin region extracting process for each frame constituting the video, and sequentially transmits the coordinates of the skin region in each frame to the video pulse wave extracting unit 123.

<Video Pulse Wave Extracting Unit>

The video pulse wave extracting unit 123 extracts a video pulse wave representing a temporal change in the brightness value from a video signal in the skin region of the subject extracted by the skin region extracting unit 122. The video pulse wave extracting unit 123 outputs the video pulse wave information indicating the extracted video pulse wave to the distortion calculating unit 130.

Light irradiated on the skin of the subject is scattered and absorbed by the subcutaneous tissue, and a part of the light is reflected back to the surface of the skin. At this time, the intensity of reflected light fluctuates depending on the subcutaneous blood flow rate because the light is absorbed by the hemoglobin contained in the blood flow. In particular, the absorption property of hemoglobin exhibits high absorption peak around 500-600 nm. This light absorption property corresponds to the frequency band of green light observed by the video camera. Therefore, when the hemoglobin contained in the blood flow in the peripheral blood increases as the heart contracts, the brightness value of the green component contained in the video decreases. Accordingly, the brightness value extracted by the video pulse wave extracting unit 123 is not particularly limited, but it is preferable to extract the brightness value of the green light from the viewpoint of extracting the video pulse wave appropriately reflecting the fluctuation in the blood flow. The present embodiment exemplifies a case where the brightness value of green light is extracted.

The video pulse wave extracting unit 123 extracts the brightness value of the green light by applying a green filter to the skin region of each frame of the video, or by using the brightness value of "G (green)". Then, the video pulse wave extracting unit 123 extracts the video pulse wave having a temporal change curve by calculating the average values of the brightness value of the green light for each frame. The video pulse wave extracting unit 123 may carry out, before extracting the brightness value of the green light from the video signal, smoothing of the image and removing artificial impulsive noise generated in the camera itself serving as the video obtaining device 300.

<Distortion Calculating Unit>

The distortion calculating unit 130 calculates a waveform distortion obtained from the heartbeat basic component and the heartbeat high-frequency component included in the video pulse wave. The distortion calculating unit 130 according to the present embodiment includes a filtering unit 131, a feature point detecting unit 132, a vertex detecting unit 133, and a difference calculation unit 134. The video pulse wave information output from the video pulse wave extracting unit 123 is input into the filtering unit 131 and the vertex detecting unit 133. In the present embodiment, the distortion calculation unit 130 calculates the difference $T_{BH}$ in the time domain as the waveform distortion. Each of the elements will be described below.

<Filtering Unit>

The filtering unit 131 performs a filtering process for passing a frequency component of the heartbeat frequency band on the video pulse wave. For example, the filtering process can use a band-pass filtering process that passes a band including a frequency component of a heartbeat frequency band, and a low-pass filtering process that passes a band of a frequency component of the heartbeat frequency band and a band of a frequency component lower than the heartbeat frequency band. The heartbeat frequency band is a band corresponding to the frequency of the heartbeat of a subject, and can be appropriately set for each subject. For example, when the subject is resting, the heartbeat frequency band is usually between 0.7-1.8 Hz, preferably between 0.9-1.5 Hz. In a state where the subject is exercising or after exercising, or in a state in which the subject is tense or excited, and the like, the heartbeat frequency band is usually 1.0-3.5 Hz, preferably 1.5-3.0 Hz. The filtering unit 131, by performing the filtering process, obtains the basic wave from the video pulse wave. The filtering unit 131 outputs the video pulse wave information indicating the basic wave to the feature point detecting unit 132.

<Feature Point Detecting Unit>

The feature detecting unit 132, from the video pulse wave information output from the filtering unit 131, detects a feature point of the basic wave. In the present embodiment, the feature detecting unit 132 detects a local minimum point of the basic wave as a feature point. Usually, the basic wave exhibits a sinusoidal pattern in which the intensity cyclically repeats the local maximum value and the local minimum value. A local minimum point is a point that has a minimum value in one cycle of the basic wave. A local minimum point can be detected in a known method. For example, by comparing the change in the intensity of the basic wave in time series, a point of time at which the change turns from decrease to increase can be detected as the local minimum value. The feature point detecting unit 132 outputs a feature point to the difference calculation unit 134.

<Vertex Detecting Unit>

The vertex detecting unit 133 detects a vertex of the video pulse wave from the video pulse wave information. In the present embodiment, the vertex of the end diastole segment of the video pulse wave is detected as the vertex. Usually, the intensity of the video pulse wave increases from the initial systole, exhibits a maximum value, and starts to decrease in the late systole in accordance with the cardiac cycle. Then the intensity continues to decrease from the initial diastole and exhibits a minimum value at the end diastole. Consequently, the intensity exhibits a periodic pattern. The vertex is a point of a downward peak occurring in the end diastole of the cardiac cycle in one cycle of the video pulse wave. The detection of the vertex can be performed using a known manner, for example, as described with reference to FIG. 6(*c*), by using line fitting. Alternatively, a vertex can be detected by using a polynomial filter. The vertex detection unit 133 outputs the vertex to the difference calculation unit 134.

<Difference Calculating Unit>

The difference calculating unit 134 calculates a time difference between the feature point detected by the feature point detecting unit 132 and the vertex detected by the vertex detecting unit 133. At this time, as described above with reference to FIGS. 6(*a*)-6(*d*), the difference calculating unit 134 calculates the time difference between the feature point and the vertex for each cycle corresponding to one beat of the heart. Thus, the difference computing unit 134 can calculate the difference $T_{BH}$ in the time domain. The calculation of the difference $T_{BH}$ in the time domain by the distortion calculation unit 130 described above is performed for each cycle of the video pulse waves. The difference calculation unit 134 outputs the difference $T_{BH}$ in the time domain to the measuring unit 141.

<Measuring Unit>

The measuring unit 141 measures a fluctuation in a blood pressure of a subject based on a waveform distortion calculated by the distortion calculation unit 130. In the present embodiment, the fluctuation in blood pressure of the subject is measured on the basis of the difference $T_{BH}$ in the time domain calculated by the difference calculation unit 134. Specifically, the measuring unit 141 measures the fluctuation in the blood pressure of the subject according to an increase or decrease in the differential $T_{BH}$ in the time domain. Here, the measuring unit 141 measures an increase in the difference $T_{BH}$ in the time domain as a decline in the blood pressure, and measures a decrease in the difference $T_{BH}$ as a rise in the blood pressure. That is, when the difference $T_{BH}$ in the time domain is increasing, the measuring unit 141 determines that the blood pressure is declining, and when the difference $T_{BH}$ in the time domain is decreasing, the measuring unit 141 determines that the blood pressure is rising. As described above, in the present embodiment, a fluctuation in the blood pressure can be measured by using a negative correlation between the difference $T_{BH}$ and a fluctuation in the blood pressure in the time domain. The measuring unit 141 outputs the measuring result of a fluctuation in a blood pressure to the output controlling unit 151. Furthermore, the measuring unit 141 outputs the measuring result of a fluctuation in a blood pressure to the measuring result storing unit 172. The measuring result storing unit 172 then stores the inputted measuring result of a fluctuation in the blood pressure therein.

The measuring unit 141 may derive (estimate) the absolute value of the blood pressure value from the waveform distortion in addition to the measurement of a fluctuation in the blood pressure using the waveform distortion described above. The derivation of the blood pressure value from a waveform distortion can be performed on the basis of the reference information.

The measuring unit 141 can calculate the blood pressure value from the waveform distortion by reading the association information from the reference information storing unit 173 and reading the blood pressure value associated with the waveform distortion. At this time, for example, the blood pressure value may be estimated from the waveform distortion by reading the association information created for each subject. Alternatively, the blood pressure value may be estimated from the waveform distortion by reading the association information of the category that the subject belongs to from the association information created according to categories of age and gender of the subjects. Alternatively, multiple pieces of association information created for each of various environments such as a measurement location and a measurement time may be stored, and the measuring unit 141 may read the association information corresponding to the current environment and estimate the blood pressure value from the waveform distortion.

The measuring unit 141 reads the conversion information from the reference information storing unit 173, and converts the waveform distortion into a blood pressure value using the conversion information. At this time, likewise the association information, the conversion information created for each subject, the conversion information created according to categories of age and gender of the subjects, and the conversion information created for each of various environments may be read appropriately to convert the waveform distortion into a blood pressure value.

Alternatively, the measuring unit 141 may calculate the blood pressure value from the waveform distortion through multiple regression analysis using a multiple regression equation. In this multiple regression equation, for example, the blood pressure value of the subject can be used as an objective variable, and the waveform distortion, the heart rate, and the pulse wave amplitude of the subject can be used as explanatory variables. In this instance, the measuring unit 141 can calculate the blood pressure value by reading, from the reference information storing unit 173, the regression coefficient and the determination coefficient of the multiple regression equation calculated in advance and inputting the waveform distortion, the blood pressure value, the heart rate, and the pulse wave amplitudes of the subject into the multiple regression equation using the read coefficients. Information such as a blood pressure value, a heart rate, and a pulse wave amplitude used in the multiple regression analysis may be stored in the reference information storing unit 173, and the measuring unit 141 may read the information from the reference information storing unit 173 and use the read information for multiple regression analysis.

<Output Controlling Unit>

The output controlling unit 151 outputs the output information based on the measuring result of a fluctuation in a blood pressure by the measuring unit 141 to the outputting device 400, and controls the outputting device 400 to display the control information. The output controlling unit 151 may control the outputting device 400 to display the video of the video signal obtained by the video obtaining device 300, the skin region extracted by the skin region extracting unit 122, and the waveform distortion calculated by the distortion calculation unit 130.

[1-2. Methods]

Figure 7:
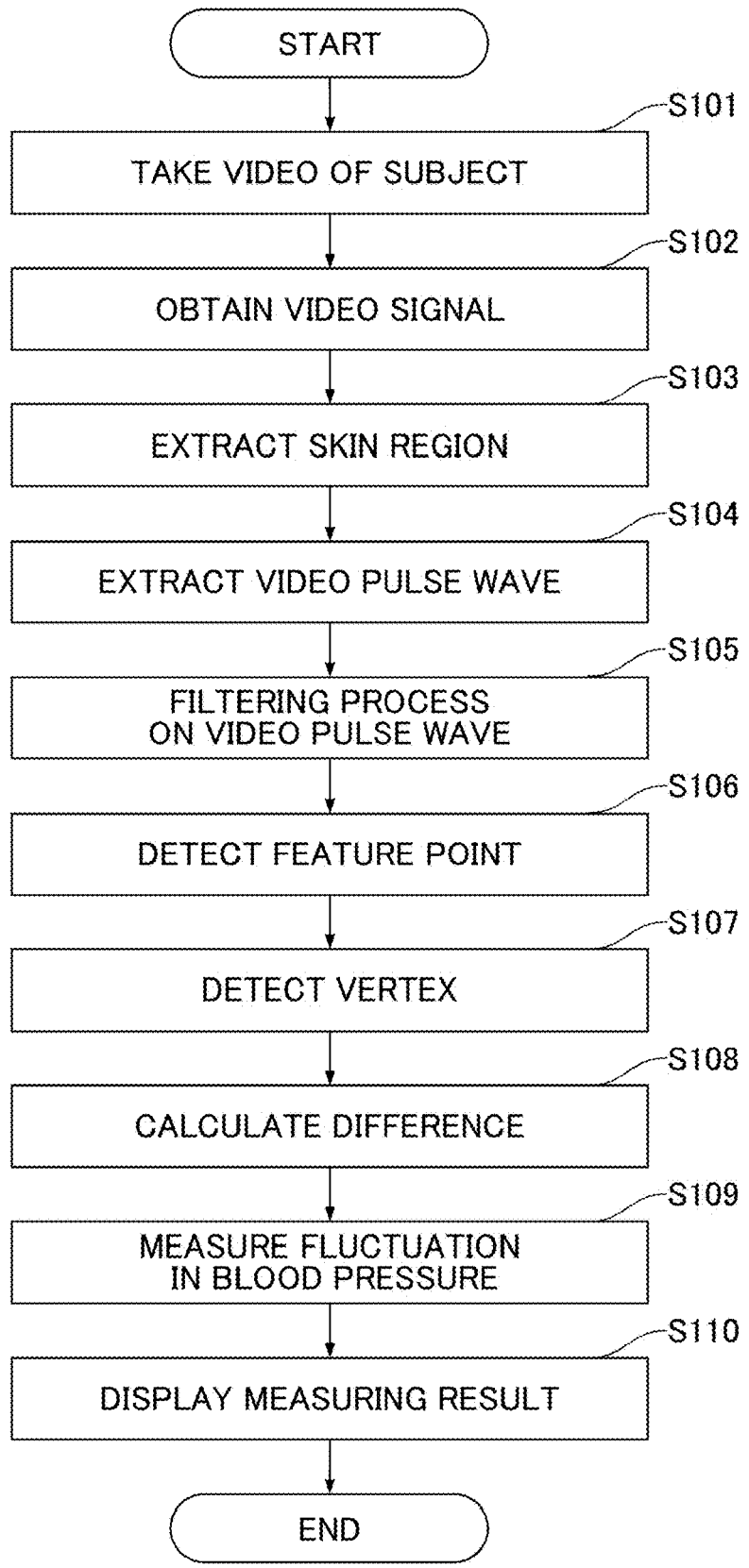
FIG. 7 is a flowchart illustrating an example of a process in a biological information measuring apparatus according to the first embodiment.

The processing of the biological information measuring device 100 and the method for measuring biological information performed by using the biological information measuring apparatus 100 will be described with reference to FIG. 7.

First, a video of a subject is taken by the video obtaining device 300 to obtain a video signal (Step S101). In this embodiment, a video camera (TGX02c, product of Baumer) was used as a video obtaining device 300. This video camera has a pixel number of 400×400 px and a frame rate of 120 fps. A video of the face and right palm of the subject sitting against the video camera was taken. At this time, the video was taken under a state where the face and the right hand were placed on respective mounts for fixing them and also the palm of the hand were facing the camera and the right hand arranged on the right side of the face. The distance between the video camera and the right hand of the subject was set to be 100 cm apart. In addition, the video was taken under a state where the white LED light source was directed from a near point of the camera to the subject and the light was irradiated such that the illuminance of the face and the right palm was 1000 lux.

Subjects are 20 healthy adult males with a mean age of 22.8+/−1.1 (21.7-23.9). In order to confirm the influence on the measurement by changing the blood pressure, the subjects performed breath holding operation by the Valsalva method at the time of video taking. Specifically, rest of 1 minute, operation by the Valsalva method of 1 minute, and rest of 3 minutes were sequentially performed during taking the video, and the video taking was conducted for 5 minutes in total. This test was repeated twice to obtain data of 10 minutes in total.

During the video taking, a continuous blood pressure monitor (PORTAPRES Model-2, Product of Finapres Medical Systems) was worn on the left second finger of each subject to measure the blood pressure. In addition, signals measured with a blood pressure monitor were converted by an A/D converter (MP150, product of BIPAC System Co.), and thereby the blood pressure during systole was recorded. This A/D converter has a sampling frequency of 1 kHz and a resolution of 16 bits.

The video signal obtaining unit 121 obtains the video signal by receiving the video signal obtained in Step S101 from the video obtaining device 300 (Step S102).

The skin region extracting unit 122 extracts a skin region of the subject included in the video of the video signal obtained in Step S102 (Step S103). In this example, the ROIs were designated in the regions of the palm, the forehead, and the right cheek of the subject, thereby extracting the designated regions as skin regions.

The video pulse wave extracting unit 123 extracts a video pulse wave representing a temporal change in brightness value from the video signal of the skin region extracted in Step S103 (Step S104). In this example, the video pulse wave was extracted by calculating the average value of the brightness values of the green components of the coordinates included in the skin region of each frame of the video signal.

The filtering unit 131 performs a filtering process on the video pulse wave extracted in Step S104 to pass the frequency components of the heartbeat frequency band, thereby obtaining a basic wave (Step S105). In this example, a band-pass filtering process is applied to pass frequency components of from 0.7-1.8 Hz.

Furthermore, the feature point detecting unit 132 detects, from the basic wave obtained in Step S105, detects the local minimum point serving as a feature point (Step S106).

The vertex detecting unit 133 detects the vertex of the end diastolic segment of the video pulse wave extracted from the video pulse wave extracted in Step S104 (Step S107). In this example, the vertex was detected by detecting an end diastolic point by means of line fitting.

Subsequently, the difference calculating unit 134 calculates the waveform distortion between the heartbeat basic component and the heartbeat high-frequency component. Specifically, the difference $T_{BH}$ in the time domain is calculated by calculating the time difference between the local minimum point of the basic wave detected in Step S106 and the end diastolic point of the video pulse wave detected in Step S107 (Step S108; distortion calculating step).

Further, the measuring unit 141 measures a fluctuation in a blood pressure of the subject based on the waveform distortion calculated by the difference calculation unit 134 (Step S109; measuring step). In this example, the fluctuation in the blood pressure is measured by using the negative correlations between the difference $T_{BH}$ in the time domain calculated in the Step S108 and a fluctuation in the blood pressure.

Further, the output controlling unit 151 controls the outputting device 400 to display of the differential $T_{BH}$ in the time domain calculated in Step S108, so that the outputting device 400 displays a graph illustrating the temporal change in the difference $T_{BH}$ in the time domain as a measuring result (Step S110).

The measuring result of a single subject according to the present example are shown in FIGS. 8(a)-8(c). In FIGS. 8(a)-8(c), a systolic blood pressure (SBP) is expressed by a thick solid line in the upper portions of the graphs. The difference $T_{BH}$ in the time domain is expressed by a thin solid line in the lower portions of the graphs, and the trend of the difference $T_{BH}$ in the time domain is expressed by a dashed line in the lower portions of the graphs. In addition, the horizontal axis represents the measurement time (seconds) (Time[s]), and the vertical axis represents the measuring values of the systolic blood pressure and the length (seconds) of the difference $T_{BH}$ in the time domain. FIGS. 8(a)-8(c) show the measuring results of the forehead part (forehead), the right palm (right palm) of the right hand, and the right cheek (right cheek), respectively.

Thereafter, the same is applied to FIG. 9, FIG. 10, and FIGS. 15(a)-15(c).

Figure 8:
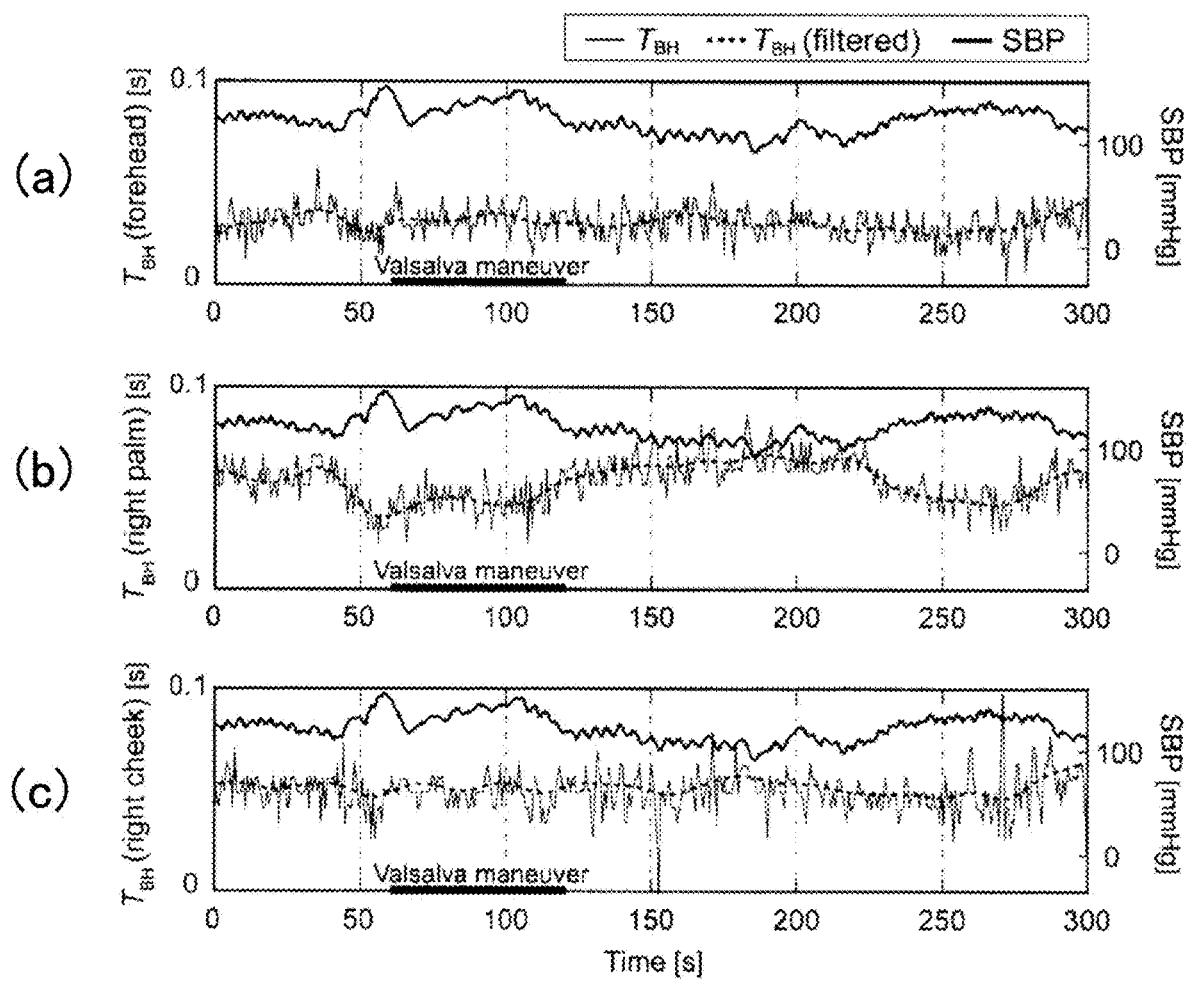
FIG. 8 are graphs illustrating measuring results by a biological information measuring apparatus according to the first embodiment, (a) illustrating a measuring result on the forehead portion, (b) illustrating a measuring result on the right palm, and (c) illustrating a measuring result on the right cheek.

FIGS. 8(a)-8(c) exhibit changes in systolic blood pressure in response to the operation of the Valsalva method at 60-120 seconds. From FIGS. 8(a)-8 (c), it can be understood that the difference $T_{BH}$ in the time-domain tends to show an opposite change to the systolic blood pressure. Above all, as is clear from FIG. 8(b), the difference $T_{BH}$ in the time-domain measured by the right palm shows a change opposite to the systolic blood pressure. Here, the average value of the partial correlation coefficients between the difference $T_{BH}$ in the time domain and the systolic blood pressure was about 0.2 higher than the average value of the partial correlation coefficients between the difference $T_{BH}$ in the time domain and the heart rate. From the above, it can be said that the change in the difference $T_{BH}$ in the time domain mainly depends on the fluctuation in the blood pressure. Further, although the waveform of the difference $T_{BH}$ in the time domain contains a high-frequency noise, the Mayer wave (cycle: about 0.1 Hz) and the respiratory fluctuation (cycle: about 0.3 Hz) observed in the waveform of the systolic blood pressure were not reflected in the waveform of the difference $T_{BH}$ in the time domain.

Figure 9:
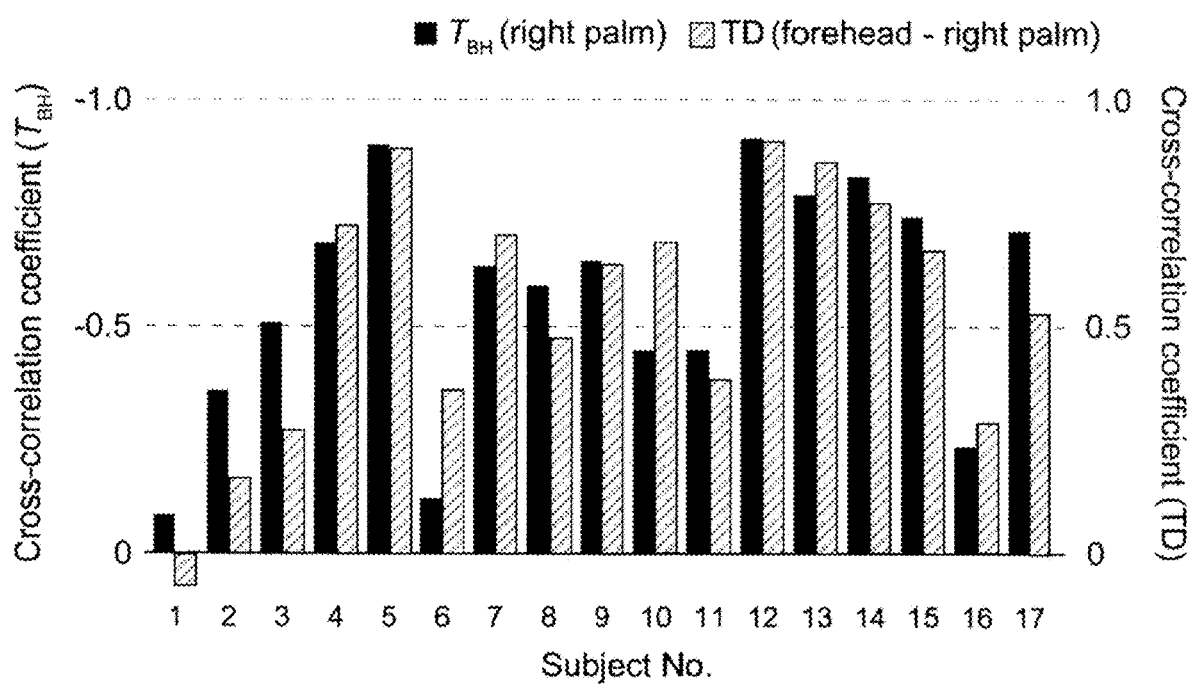
FIG. 9 is a graph illustrating the cross-correlation coefficient between measuring results by the biological information measuring apparatus according to the first embodiment and the systolic blood pressure of each subject.

In FIG. 9, the cross-correlation coefficients (Cross-correlation coefficient) between the systolic blood pressure and the difference $T_{BH}$ in the time domain measured on the right palm for each of the subjects numbered 1 to 17 (Subject No. 1-17) that could be analyzed are shown in black bars. For reference, the cross-correlation coefficients between a systolic blood pressure and a pulse transit time difference (TD) obtained from the multiple ROIs are indicated by gray-hatched bars, each gray-hatched bar being disposed right next to each black bar. The pulse transit time difference represents a time difference between the arrival times of the two video pulse waves measured at the forehead and the right palm of the subject. A pulse transit time difference is known to exhibit a high cross-correlation coefficient with a blood pressure. The pulse transit time difference can be measured by a known technique, and for example, can be performed in the same manner as the measuring of dPTT described in Japanese Patent Application Laid-Open No. 2016-190022, so the explanation thereof is omitted here. Among the 20 subjects, one subject experienced an arrhythmia, and two subjects experienced an error in the device, so FIG. 9 shows the cross-correlation coefficients of the 17 subjects from the subject numbers 1 to 17.

As shown in FIG. 9, the cross-correlation coefficient between the systolic blood pressure and the pulse transit time difference was mainly positive. In contrast, the cross-correlation coefficient between the systolic blood pressure and the difference $T_{BH}$ in the time domain was negative. Furthermore, the difference $T_{BH}$ in the time domain and the pulse transit time difference showed almost the same degree of correlations with the systolic blood pressure, although differing in positiveness and negativeness.

Figure 10:
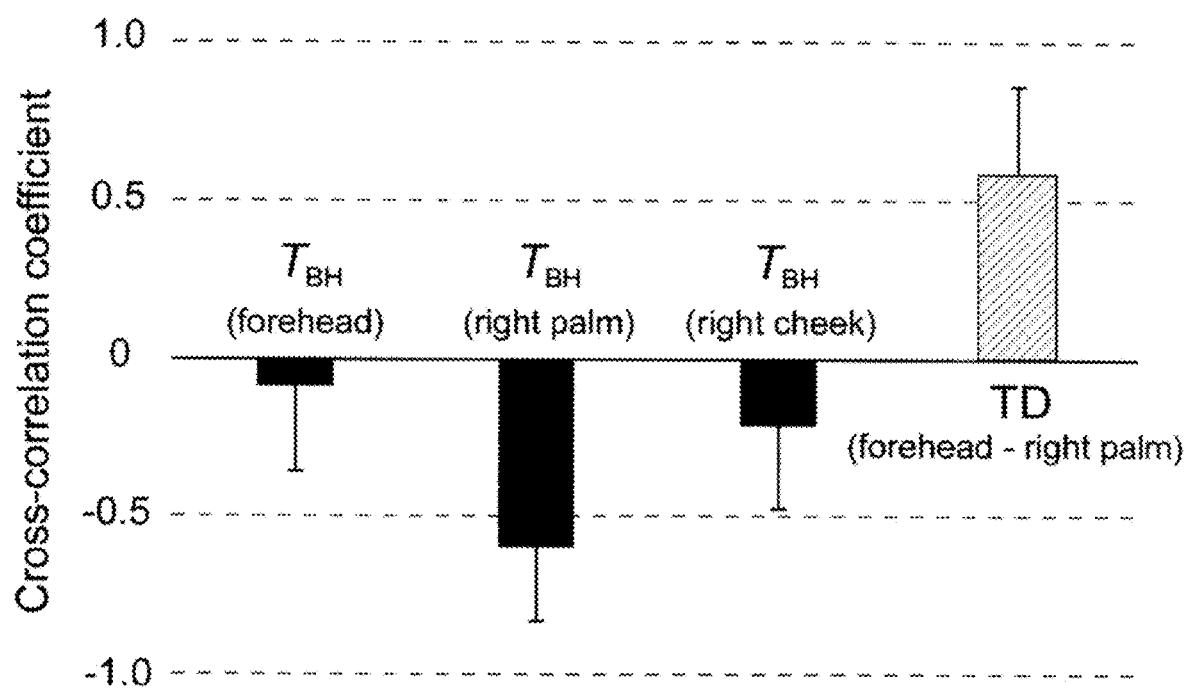
FIG. 10 is a graph illustrating an average of the cross-correlation coefficients between measuring results by the biological information measuring apparatus according to the first embodiment and the systolic blood pressures.

FIG. 10 shows values obtained by averaging the cross-correlation coefficients between the systolic blood pressure and the difference $T_{BH}$ in the time domain of the respective subjects. Since the subject numbered with "1" exhibited a negative cross-correlation coefficient between the systolic blood pressure and the pulse wave propagation time difference among the 17 subjects shown in FIG. 9, the average value of the 16 subjects excluding the subject numbered with "1" is shown here. Specifically, the cross-correlation coefficients represent the difference $T_{BH}$ in the time domain at different measuring parts of the forehead portion, the right palm, and the right cheek. Similarly, the cross-correlation coefficient between the systolic blood pressure and the pulse transit time difference indicates the average value of 16 subjects excluding the subject numbered with "1" among the subjects are shown in FIG. 9.

As shown in FIG. 10, the cross-correlation coefficients between the systolic blood pressure and the difference $T_{BH}$ in the time-domain showed negative correlation at all the measuring parts. Above all, the cross-correlation coefficients of the difference $T_{BH}$ in the time domain measured in the right palm showed a higher value than that between the systolic blood pressure and the pulse transmit time difference. Therefore, it was revealed that the cross-correlation coefficients showed strong correlation at the right palm.

In the measuring results in this example, it is presumed that the difference in the cross-correlation coefficient of the right palm from those of the forehead and the right cheek is related to the difference in the neuromodulation performed between the face and the extremities in the body. Here, it is known that not only the vasoconstriction by the sympathetic nerve but also the parasympathetic vasodilation occurs in the face. In contrast, only the sympathetic nervous system appears to cause vasoconstriction in the skin of the extremities. In other words, parasympathetic vasodilation may prevent a change in the video pulse waves caused by vasoconstriction by the sympathetic nervous system in the region of the face.

[1-3. Actions and Effects]

The biological information measuring apparatus 100 according to the present embodiment, which is configured as described above, can obtain the following actions and effects.

(1) In the biological information measuring apparatus 100, the distortion calculating unit 130 calculates the waveform distortion of the heartbeat basic component and the heartbeat high-frequency component included in the video pulse wave from the video signal of the predetermined part of a subject. In addition, the measuring unit 141 measures a fluctuation in a blood pressure of the subject based on the waveform distortion. As described above, the biological information measuring apparatus 100 uses the heartbeat basic component including the rate information as a substitute for the information obtained by the electrocardiographic measurement. Further, the biological information measuring apparatus 100 can measure the fluctuation in the blood pressure of the subject from the waveform distortion of the heartbeat basic component and the heartbeat high-frequency component by using the heartbeat high-frequency component including the information on the blood pressure in a frequency band higher than the heartbeat frequency band. This allows the biological information measuring apparatus 100 to easily measure the fluctuation in the blood pressure of the subject from the video signal obtained by taking a video of the body of the subject without contact with the subject. Further, the biological information measuring apparatus 100 can measure the fluctuation in the blood pressure of the subject from the video signal obtained from one part of the subject by using the waveform distortion of the video pulse wave. Therefore, for example, the requirement for simultaneously taking a video of two or more parts of the subject can be eliminated so that it is possible to more easily measure the fluctuation in the blood pressure. Therefore, it is possible to measure the fluctuation in the blood pressure by taking a video of a part of the body of the subject in a state in which the subject performs daily operation, a state where the subject is resting, or the like. In addition, even in a case where it is difficult to maintain a desired posture because the subject is performing some kind of operation such as driving a vehicle, for example, it is possible to measure the fluctuation in the blood pressure by taking a video of a part of the body of the subject.

(2) At this time, the measuring unit 141 measures an increase in waveform distortion as a decline in blood pressure, and conversely measures a decrease in waveform distortion as a rise in blood pressure. As described with reference to FIGS. 5(a), 5(b), and 6(a)-6(c), the measuring unit 141, can measure the fluctuation in the blood pressure using the negative correlation between the waveform distortion and the fluctuation in the blood pressure.

(3) In the present embodiment, the waveform distortion is represented by the difference between the heartbeat basic component and the heartbeat high-frequency component in the time domain. The difference calculating unit 134 calculates the time difference (the difference $T_{BH}$ in the time domain) between the feature point of the basic wave and the vertex of the end diastolic segment of the video pulse waves. As described above, the biological information measuring device 100 can measure the fluctuation in blood pressure by using the difference $T_{BH}$ in the time-domain. As a result, the distortion calculation unit 130 can calculate the waveform distortion and measure a fluctuation in a blood pressure by a method having a relatively low calculation load. Therefore, it is possible to measure a fluctuation in the blood pressure in real time.

(4) Further, the measuring unit 141 calculates a blood pressure value corresponding to the waveform distortion based on the association information between the waveform distortion and the blood pressure value of the subject. As a result, the measuring unit 141 can measure the fluctuation in blood pressure in the form of an absolute value.

(5) In addition, the measuring unit 141 calculates the blood pressure value by multiple regression analysis using a multiple regression equation that uses the blood pressure value of the subject as an objective variable and the waveform distortion, the heart rate, and the pulse wave amplitude as explanatory variables. This can improve the accuracy of the absolute value of the blood pressure measured by the measuring unit 141.

(6) Here, in the biological information measuring device 100, the video pulse wave information includes the temporal change in the brightness value included in the video signal of the part where the peripheral arteriole rises peripheral blood vessel resistance under control of the sympathetic nervous system when the blood pressure rises. That is, the biological information measuring apparatus 100 takes a video of a part where the peripheral arteriole is innervated by the sympathetic nerve to rise the peripheral vascular resistance when the blood pressure rises, and calculates the waveform distortion from the video signal of this part. Accordingly, the accuracy of the measurement of the fluctuation in the blood pressure by the measuring unit 141 can be further improved, since the change is difficult to be suppressed due to the vasodilation of the parasympathetic nervous system with respect to the change in the video pulse wave caused by the vasoconstriction by the sympathetic nervous system.

(7) Further, in the biological information measuring apparatus 100, the video pulse wave information includes a temporal change in the brightness value included in the video signal of a palm of the subject. That is, the biological information measuring apparatus 100 takes a video of a palm of the subject, and calculates waveform distortion from the video signal of the palm. The influence of vasoconstriction by the sympathetic nervous system is dominant in peripheral sites such as the hand, without being affected by parasympathetic vasodilation. Therefore, use of the video signal of a palm makes it possible to further improve the accuracy in measuring a fluctuation in a blood pressure.

[1-4. Miscellaneous]

The light reflectivity may be different with measuring part and the body color of the measuring part of the subject, and the brightness value included in the video signal obtained by the video obtaining device 300 may be different. At this time, if the brightness value is excessively low, excessively high, or fluctuates during taking a video, the intensity of the video pulse wave is not stabilized, which makes it difficult to appropriately measure a fluctuation in a blood pressure. For this reason, the biological information measuring apparatus 100 may be provided with illumination that irradiating the measuring part of the subject with light. In addition, the biological information measuring apparatus 100 may be provided with an illuminance sensor that measures the illuminance of the measuring part of the subject. Furthermore, the biological information measuring apparatus 100 may include a feedback controlling unit that controls the intensity of light emitted from illumination such that the illuminance of the measuring part becomes constant on the basis of the illuminance of the measuring part of the subject measured by the illuminance sensor.

In the above embodiment, a case where the biological information measuring apparatus 100 includes the video obtaining device 300, and the video signal obtaining unit 121 obtains the video signal obtained by the video obtaining device 300 to calculate a waveform distortion and measure a fluctuation in a blood pressure has been exemplified. The configuration of the biological information measuring apparatus 100 is not limited to this, and may alternatively be a system in which the video signal obtaining unit 121 obtains a video signal via a network, calculates waveform distortion from the video signal, and measures a fluctuation in a blood pressure. In this alternative, for example, a video signal obtained by a video camera provided for the purpose of watching a subject, nursing care, observation, surveillance, or crime prevention, a PC including a video camera, a smart phone, a tablet terminal, or the like can be transmitted to the video signal obtaining unit 121.

2. Second Embodiment

A biological information measuring apparatus according to the second embodiment will be described with reference to FIGS. 1 and 11-15. Hereinafter, in the description of the second embodiment, this second embodiment is also simply referred to as the present embodiment. In contrast to the biological information measuring device 100 according to the first embodiment, which includes the distortion calculating unit 130, the second embodiment is different in the point that the biological information measuring apparatus 100 includes a distortion calculating unit 136 having a different function from the distortion calculating unit 130 of the first embodiment. Furthermore, in the present embodiment, the waveform distortion is calculated as the ratio of the heartbeat basic component and the heartbeat high-frequency component in the frequency domain. Then, the biological information measuring device according to the present embodiment measures the fluctuation in the blood pressure from the calculated ratio in the frequency domain. A part of the configuration of the biological information measuring apparatus according to the present embodiment is configured in the same manner as the biological information measuring apparatus according to the first embodiment described above, and the description of the same components as those of the biological information measuring apparatus according to the first embodiment is omitted, and the same reference numerals are used to explain the same.

[2-1. Configuration]

[2-1-1. Hardware Configuration]

As shown in FIG. 1, the biological information measuring apparatus 101 according to the present embodiment includes an information processing apparatus 200, similarly to the biological information measuring apparatus 100. The biological information measurement apparatus 101 further includes a video obtaining device 300 and an outputting device 400.

[2-1-2. Functional Configuration]

Figure 11:
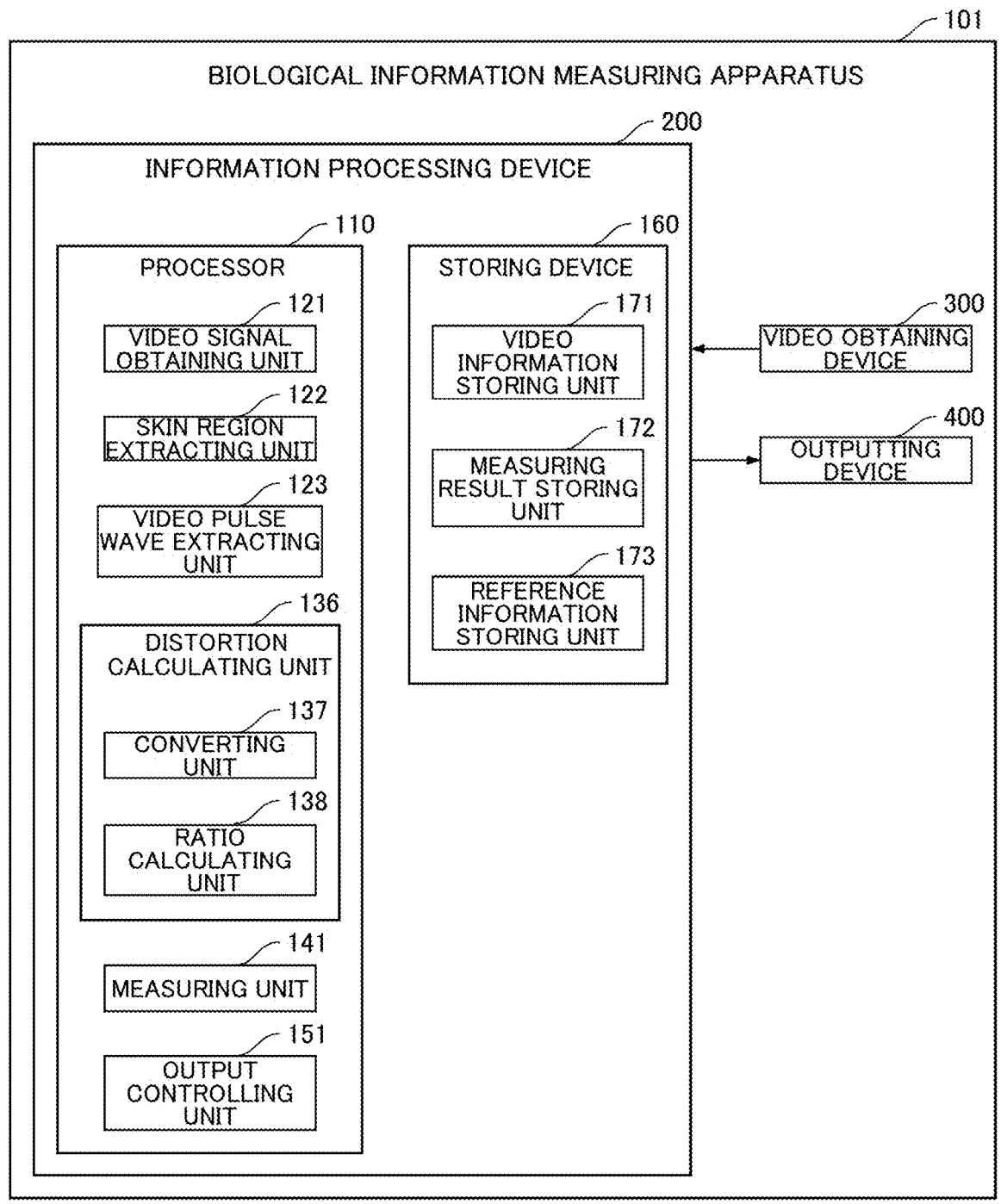
FIG. 11 is a block diagram illustrating an example of the functional configuration of a biological information measuring apparatus according to a second embodiment.

As shown in FIG. 11, being functionally exhibited, the biological information measuring apparatus 101 includes an information processing device 200, a video obtaining device 300, and an output device 400 likewise the biological information measuring apparatus 100. Further, being functionally represented, the information processing device 200 includes a processor 110 and a storing unit 160.

<Storing Unit>

The storing unit 160 previously stores programs to function, when being executed by CPU10, as the video signal obtaining unit 121, a skin region extracting unit 122, a video pulse wave extracting unit 123, the distortion calculating unit 136, a measuring unit 141, and an output controlling unit 151 of the processor 110 to be described below.

<Processor>

As shown in FIG. 11, the processor 110 functions as the video signal obtaining unit 121, the skin region extracting unit 122, the video pulse wave extracting unit 123, the distortion calculating unit 136, the measuring unit 141, and the output controlling unit 151.

[2-1-3. Processor]

<Estimating of Fluctuation in Blood Pressure>

The principle of estimating a fluctuation in the blood pressure using the waveform distortion will now be described. In the present embodiment, a case where the waveform distortion is represented by the ratio between the heartbeat basic component and the heartbeat high-frequency component in the frequency domain will be described.

Figure 12:
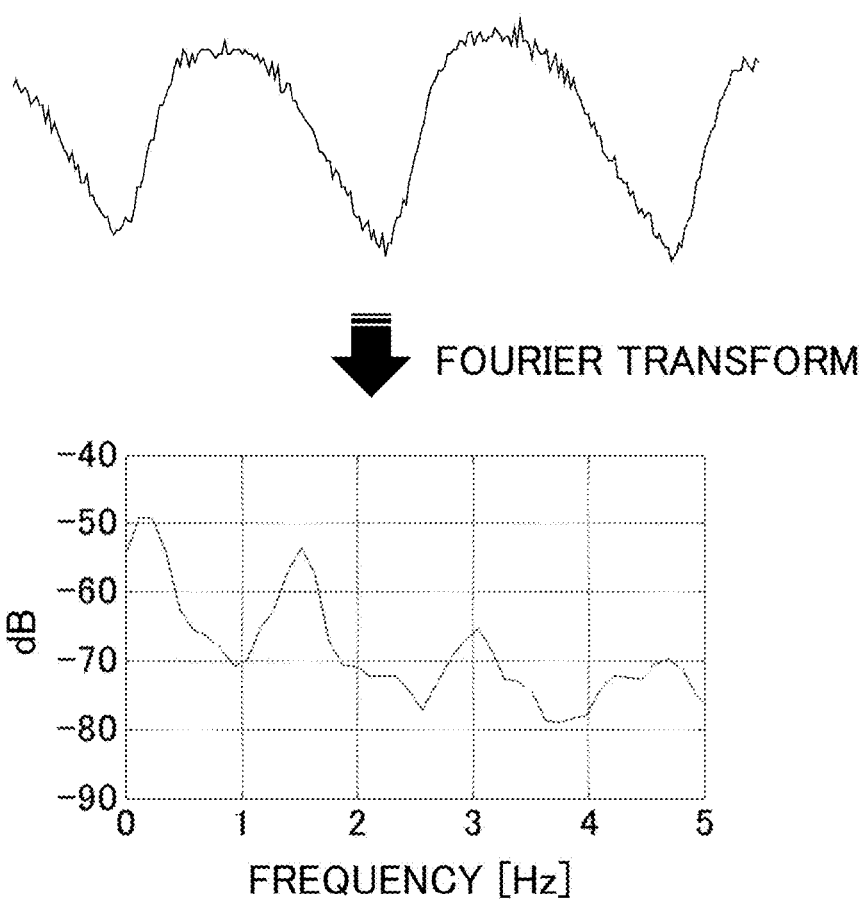
FIG. 12 is a diagram illustrating the relationship between the time domain and the frequency domain of a video pulse wave.

As shown in FIG. 12, a video pulse wave can be converted from the time domain to the frequency domain by Fourier transform. In the frequency domain, a video pulse wave can be expressed as a superposition of sinusoidal waves having various frequencies. This means that, Fourier transform on the video pulse wave, makes it possible to express the video pulse wave by the Fourier series f(x) represented by the following expression (11).

$$f(x) = \frac{1}{2}a_0 + \sum_{n=1}^{\infty} a_n \cos(nx) + \sum_{n=1}^{\infty} b_n \sin(nx) \qquad (11)$$

(In expression (11), the variables $a_0$, $a_n$, $b_n$ represent the Fourier coefficients.)

Figure 13:
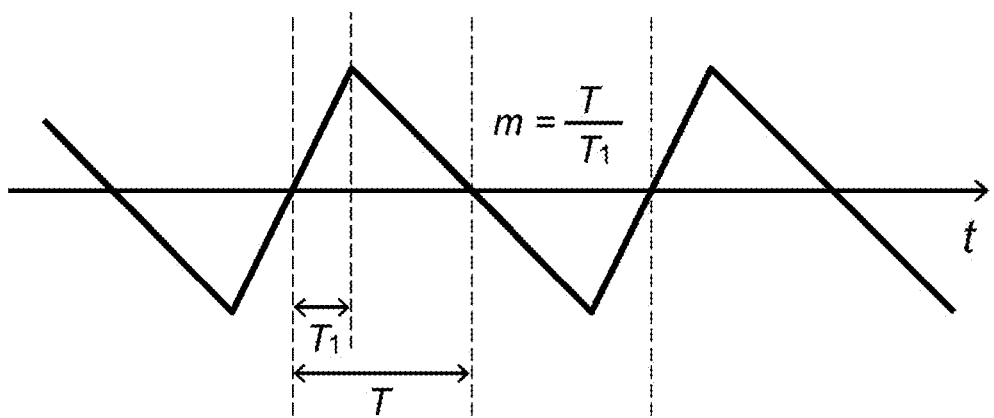
FIG. 13 is a graph illustrating a triangle wave and waveform distortion.

Here, FIG. 13 is represents a change in time (t) of an asymmetric triangle wave having a period of 2T and the position of the vertex is 1/m of the half period T ($T_1$). The symbol m (=T/$T_1$) indicates the ratio of the rising part and declining part of the triangle wave.

Then, the triangle wave shown in FIG. 13 can be expressed by $f_m$ (x) represented by the following Expression (12).

$$f_m(x) = \begin{cases} \dfrac{mx}{L} & \text{for } 0 \leq x \leq \dfrac{L}{m} \\ 1 - \dfrac{m}{(m-1)L}\left(x - \dfrac{L}{m}\right) & \text{for } \dfrac{L}{m} \leq x \leq 2L - \dfrac{L}{m} \\ \dfrac{m}{L}(x - 2L) & \text{for } 2L - \dfrac{L}{m} \leq x \leq 2L \end{cases} \qquad (12)$$

The Fourier coefficients $a_0$, $a_n$, $b_n$ can be expressed by the following Expressions (13)-(15).

$$a_0 = 0 \qquad (13)$$

$$a_n = 0 \qquad (14)$$

$$b_n = -\frac{2(-1)^n m^2}{n^2(m-1)\pi^2} \sin\left[\frac{n(m-1)\pi}{m}\right] \qquad (15)$$

In FIG. 13, the triangle wave when m=2 can be said to be a waveform free from distortion. On the other hand, as m increase to be larger than 2, the distortion of the triangle wave increases. Thus, as the value of m increases, the triangle wave more deviates from the waveform of m=2, the Fourier coefficient of the high-frequency component also increases.

From the above examination, the inventors have focused on the fact that the waveform distortion of the video pulse wave is reflected in the Fourier coefficient. That is, the distortion ratio $R_d$ of the video pulse waves can be represented by the following expression (16) by representing the Fourier coefficient corresponding to the heartbeat high-frequency component in the video pulse wave by $b_i$ and the Fourier coefficient corresponding to the heartbeat basic component of the video pulse wave by $b_1$.

$$R_d = \frac{\sum b_i}{\sum b_j} \qquad (16)$$

As shown in Expression (16), the distortion ratio $R_d$ is the ratio of the sum of the Fourier coefficient $b_i$ of the heartbeat high-frequency component to the sum $b_j$ of the Fourier coefficient of the heartbeat basic component. A small distortion ratio $R_d$ represents a state where the waveform distortion is small like a case where m=2 described above. On the other hand, a large distortion ratio $R_d$ represents a state where the waveform distortion is large. The inventors of the present invention have found that there is a negative correlation between the distortion ratio $R_d$ and a fluctuation in a blood pressure. This means that, according to the present embodiment, the fluctuation in the blood pressure can be measured on the basis of the distortion ratio $R_d$ corresponding to the ratio between the heartbeat basic component in the frequency domain and the heartbeat high-frequency component in the frequency domain.

The biological information measuring apparatus 101 according to the present embodiment measures a fluctuation in a blood pressure by calculating the distortion ratio $R_d$ from the video pulse wave representing a temporal change in the brightness value of a video signal on the basis of the principles described above. Hereinafter, the process performed by the biological information measuring apparatus 101 will be described with reference to constituent elements.

<Distortion Calculating Unit>

The distortion calculation unit 136 according to the present embodiment includes a converting unit 137 and a ratio calculating unit 138. Video pulse wave information output from the video pulse wave extracting unit 123 is input into the converting unit 137. In the present embodiment, the distortion calculating unit 136 calculates the distortion ratio $R_d$ as the waveform distortion. Each of the elements will now be described below.

<Converting Unit>

The converting unit 137 performs a Fourier transform on the video pulse wave to obtain a Fourier series of the video pulse wave. Further, the converting unit 137 calculates the sum of the Fourier coefficients of each of the heartbeat basic component and the heartbeat high-frequency component by summing the coefficients of the Fourier series of the corresponding one of the heartbeat basic component and the heartbeat high-frequency component. Then, the converting unit 137 outputs the sum of the Fourier coefficients of the heartbeat basic component and the sum of the Fourier coefficients of the heartbeat high-frequency component to the ratio calculating unit 138.

<Ratio Calculating Unit>

The ratio calculating unit 138 calculates the ratio of the sum of the Fourier coefficients of the heartbeat high-frequency component to the sum of the Fourier coefficients of the heartbeat basic component. Thereby, the ratio calculating unit 138 can calculate the distortion ratio $R_d$ in the frequency domain. The ratio calculating unit 138 outputs the distortion ratio $R_d$ in the frequency domain to the measuring unit 141.

<Measuring Unit>

The measuring unit 141 measures a fluctuation in a blood pressure of the subject based on the waveform distortion calculated by the ratio calculating unit 138. In the present embodiment, the fluctuation in the blood pressure of a subject is measured on the basis of the distortion ratio $R_d$ in the frequency domain calculated by the ratio calculating unit 138. More specifically, the measuring unit 141 measures a fluctuation in a blood pressure of a subject according to an increase or a decrease in the distortion ratio $R_d$ in the frequency domain. Here, the measuring unit 141 measures an increase in the distortion ratio $R_d$ in the frequency domain as a decline in the blood pressure, and measures a decrease in the distortion ratio $R_d$ as a rise in the blood pressure. That is, the measuring unit 141 determines that the blood pressure is declining when the distortion ratio $R_d$ in the frequency domain is increasing, and determines that the blood pressure is rising when the distortion ratio $R_d$ in the frequency domain is decreasing. As described above, in the present embodiment, a fluctuation in a blood pressure can be measured by using the negative correlations between the distortion ratio $R_d$ and a fluctuation in the blood pressure in the frequency domain.

[2-2. Method]

Figure 14:
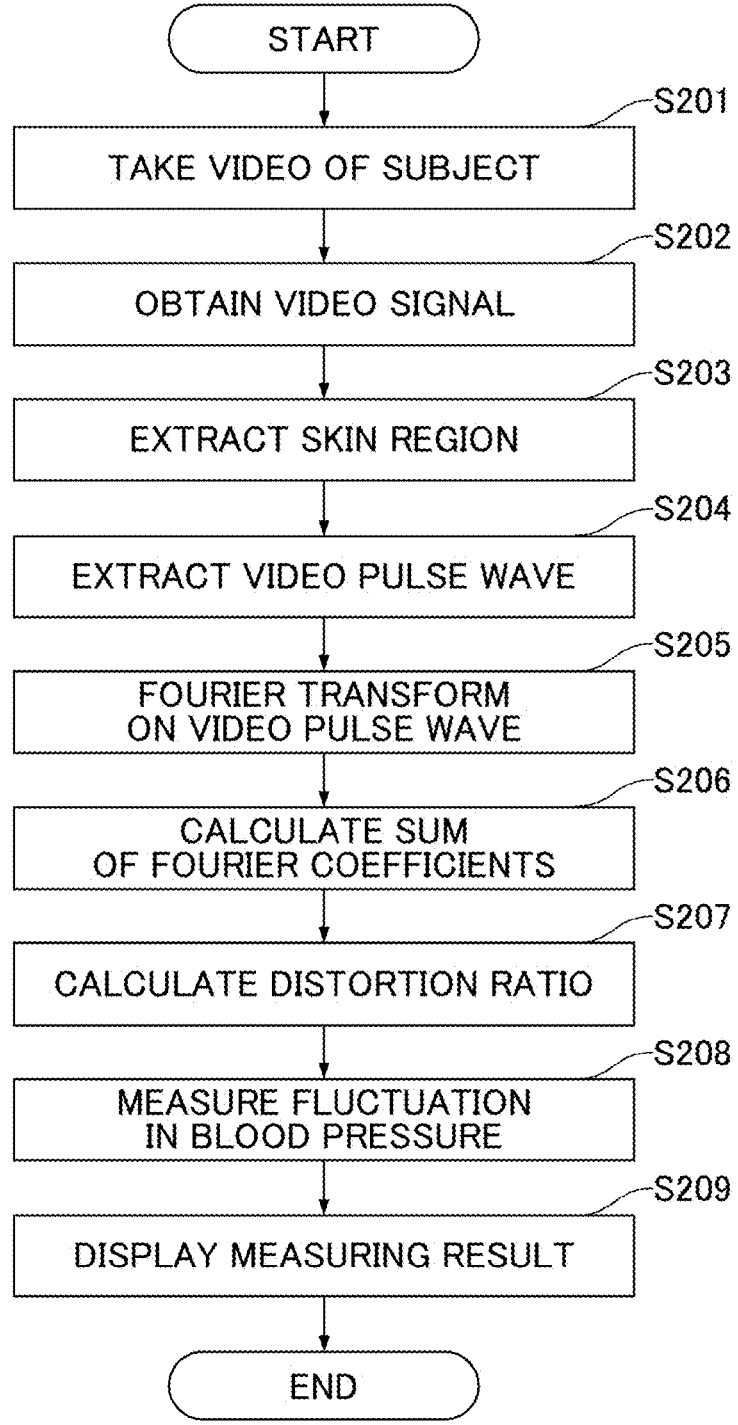
FIG. 14 is a flowchart illustrating an example of a process in a biological information measuring apparatus according to the second embodiment.

The processing of the biological information measuring device 101 and the method for measuring biological information performed by using the biological information measuring apparatus 101 will be described with reference to FIG. 14.

First, a video the subject is taken by the video obtaining device 300 to obtain a video signal (Step S201). In this example, a video camera similar to that of the first embodiment is used as the video obtaining device 300. The subject is the same as that of the first embodiment. In addition, likewise the first embodiment, video taking for 5 minutes in total was repeated twice to obtain data of 10 minutes in total. Also, likewise the first embodiment, the blood pressure of the subject was measured and the systolic blood pressure was recorded.

The video signal obtaining unit 121 obtains the video signal by receiving the video signal obtained in Step S201 from the video obtaining device 300 (Step S202).

The skin region extracting unit 122 extracts a skin region of the subject included in the video of the video signal obtained in Step S202 (Step S203). In this example, the ROIs were designated in the regions of the palm, the forehead, the right cheek, and the left cheek of the subject, thereby extracting the designated regions as skin regions.

The video pulse wave extracting unit 123 extracts a video pulse wave representing a temporal change in the brightness value from the video signal of the skin region extracted in Step S203 (Step S204). In this example, the video pulse wave was extracted by calculating the average value of the brightness values of the green components of the coordinates included in the skin region of each frame of the video signal.

The converting unit 137 performs a Fourier transform on the video pulse wave extracted in Step S204 to obtain a Fourier series of the video pulse wave (Step S205). The converting unit 137 calculates the sum of the coefficients of the Fourier series of the heartbeat basic component and that of the heartbeat high-frequency component obtained in Step S205 (Step S206). Here, a frequency component higher than the frequency component of the heartbeat frequency band is regarded as the heartbeat high-frequency component.

The ratio calculating unit 138 calculates a waveform distortion between the heartbeat basic component and the heartbeat high-frequency component. Specifically, the ratio calculating unit 138 calculates the distortion ratio $R_d$ in the frequency domain by calculating the ratio of the sum of the Fourier coefficients of the heartbeat high-frequency components to the sum of the Fourier coefficients of the heartbeat basic components that are calculated in Step S206 (Step S207).

The measuring unit 141 measures the fluctuation in the blood pressure of the subject based on the waveform distortion calculated by the ratio calculating unit 138 (Step S208). In this embodiment, the fluctuation in the blood pressure is measured by using a negative correlations in the frequency domain between the distortion ratio $R_d$ in the frequency domain calculated in Step S207 and a fluctuation in the blood pressure.

The output controlling unit 151 controls the outputting device 400 to display the distortion ratio $R_d$ in the frequency domain calculated in Step S208, so that the outputting device 400 displays a graph indicating a temporal change in the distortion ratio $R_d$ in the frequency domain as the measuring result (Step S209).

Figure 15:
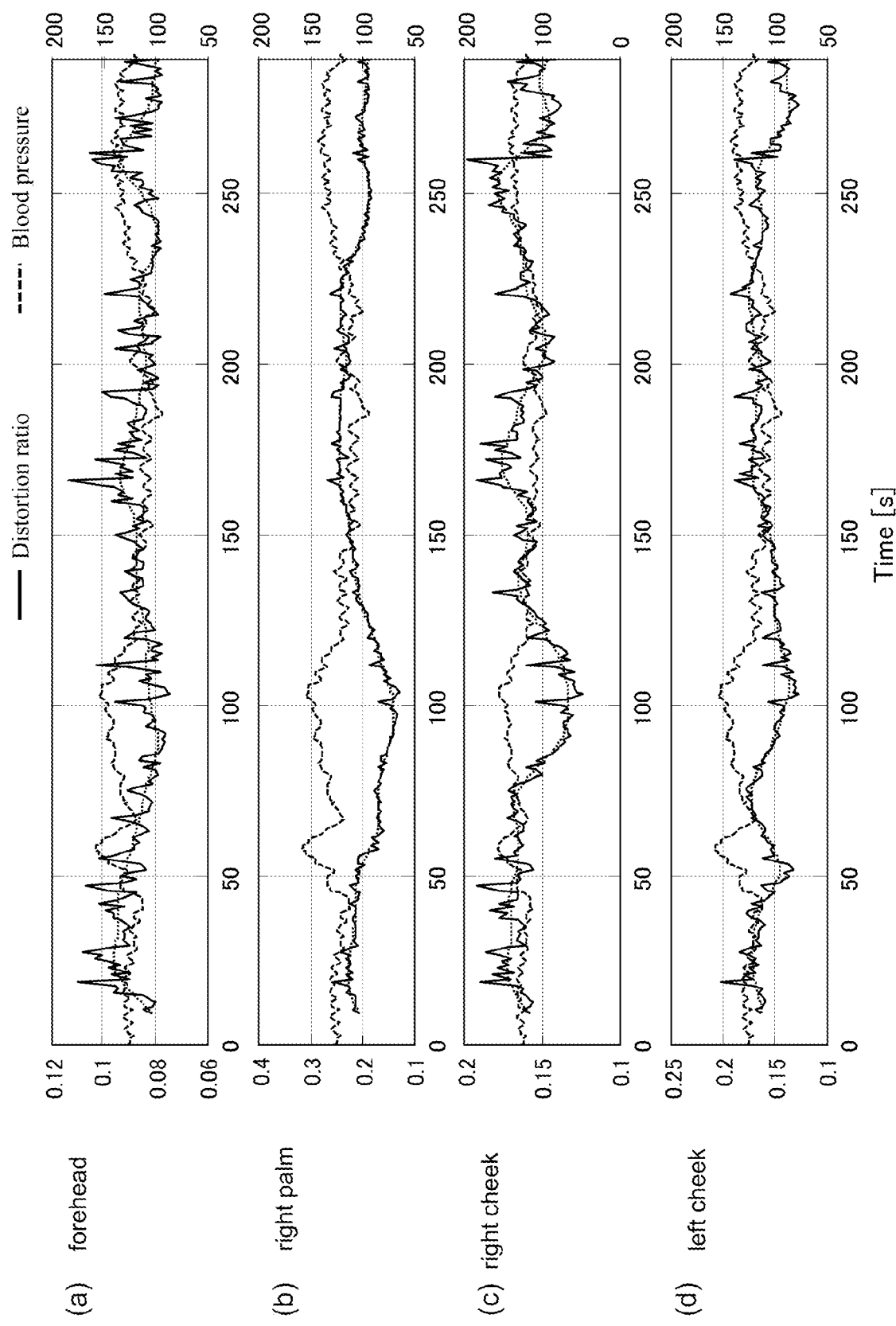
FIG. 15 are graphs illustrating measuring results by a biological information measurement apparatus according to the second embodiment, wherein (a) illustrating a measuring result on the forehead portion, (b) illustrating a measuring result on the right palm, and (c) illustrating a measuring result on the right cheek, (d) illustrating a measuring result on the left cheek.

The measuring result of a single subject according to the present example is shown in FIGS. 15(*a*)-15(*d*). In FIGS. 15(*a*)-15 (*d*), the systolic blood pressure is indicated by a dashed line. The distortion ratio $R_d$ in the frequency domain is indicated by a solid line, and the trend of the distortion ratio $R_d$ in the frequency domain is indicated by a dotted line. In addition, the horizontal axis represents the measuring time (seconds) (Time[s]), and the vertical axis represents the measuring values of the systolic blood pressure and the distortion ratio $R_d$ in the frequency domain. FIGS. 15(*a*)-15 (*d*) show the measuring results on the forehead, the right palm, the right cheek, and the left cheek, respectively.

FIGS. 15(*a*)-15(*d*) exhibit changes in the systolic blood pressure in response to respiratory arrest of the Valsalva method at 60-120 seconds. It can be seen from FIGS. 15(*a*)-15(*d*) that the distortion ratio $R_d$ in the frequency domain shows an opposite change to the systolic blood pressure, which means the ratio and the systolic blood pressure are negatively correlated with each other. Above all, from FIG. 15(*b*), the distortion ratio $R_d$ in the frequency domain measured on the right palm was observed to be most negatively correlated with the systolic blood pressure.

[2-3. Actions and Effects]

The biological information measuring apparatus 101 according to the present embodiment, which is configured as described above, can obtain the following actions and effects in addition to the effects obtained in the first embodiment described above.

In the biological information measuring device 101, the waveform distortion is represented by a ratio between the heartbeat basic component and the heartbeat high-frequency component in the frequency domain. Then, the converting unit 137 obtains the sum of the coefficients of the Fourier series of the heartbeat basic component and the sum of the coefficients of the Fourier series of the heartbeat high-frequency component. Furthermore, the ratio calculating unit 138 calculates the ratio (the distortion ratio $R_d$ in the frequency domain) of the sum of the Fourier coefficients of the heartbeat high-frequency component to the sum of the Fourier coefficients of the heartbeat basic component as a ratio in the frequency domain. As described above, the biological information measuring apparatus 101 can measure the fluctuation in blood pressure by using the distortion ratio $R_d$ in the frequency domain without using the difference in the time domain as the waveform distortion. As a result, this eliminates a requirement to detect the vertex and the feature point required for the measurement using the difference in the time domain, and makes it possible to measure the fluctuation in the blood pressure with relatively high accuracy, preventing the deterioration of the measurement accuracy of a fluctuation in a blood pressure due to the deviation of the detection positions of these vertex and the feature point.

[2-4. Miscellaneous]

In the foregoing embodiment, an example in which a frequency component higher than the frequency component of the heartbeat frequency band is used as the heartbeat high-frequency component is described. The heartbeat high-frequency component may satisfactorily include a frequency component of a frequency band higher than the heartbeat frequency band in the video pulse wave, and may alternatively use, as the heartbeat high-frequency component, a video pulse wave containing a frequency component of a frequency band higher than the heartbeat frequency band and a frequency component of the heartbeat frequency band.

All examples and conditional language provided herein are intended for pedagogical purposes to aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiment(s) of the present invention have been described in detail, it should be understood that the various changes, substitutions, alterations, and combination of the above embodiments and modifications thereof could be made hereto without departing from the spirit and scope of the invention.

What is claimed is:

1. A biological information measuring apparatus comprising;
    a video camera configured to obtain a video signal of a predetermined part of a subject;
    a memory;
    a processor having processor circuitry coupled to the memory; and
    a display configured to display information processed by the processor and information to be stored in the memory, wherein:
    the processor circuitry in the processor comprises a video signal obtainer, a video pulse wave extractor, a distortion calculator, and a measurer;
    the video camera is configured to output the video signal to the video signal obtainer;
    the video pulse wave extractor is configured to extract video pulse wave information representing a temporal change in a brightness value included in the video signal;
    the distortion calculator is configured to calculate, based on a heartbeat basic component and a second component, a waveform distortion being a change due to fluctuations in blood pressure, wherein the heartbeat basic component is obtained by filtering the extracted video pulse wave information using a filter of the distortion calculator in which the filter is set to a band corresponding to a frequency of a heartbeat of the subject and included within a range of 0.7-3.5 Hz, and the second component contains a frequency component of a frequency band higher than the heartbeat frequency band included in the video pulse information;
    the measurer is configured to measure an increase of the waveform distortion as a decline of the blood pressure and measures a decrease of the waveform distortion as a rise of the blood pressure;
    the distortion calculator comprises either:
    an element A in a case where the waveform distortion is expressed as a difference in time between the heartbeat basic component and the second component, the element A comprising:
        a feature point detector configured to detect a feature point of the heartbeat basic component;
        a vertex detector configured to detect, from the video pulse wave information, a vertex of an end diastolic segment of the video pulse wave; and
        a difference calculator configured to calculate, as the difference in time, a time difference between the feature point and the vertex, the feature point being obtained by applying a bandpass filter to a time series signal corresponding to the video pulse wave information stored in the memory; or an element B in a case where the waveform distortion is expressed as a ratio between the heartbeat basic component and the second component in a frequency domain; the element B comprising:
- a convertor configured to obtain a sum of Fourier coefficients of each of the heartbeat basic component and the second component; and
- a ratio calculator configured to calculate, as the ratio in the frequency domain, a ratio of the sum of the Fourier coefficients of the second component to the sum of the Fourier coefficients of the heartbeat basic component;

the predetermined part is a part in which an arteriole increases a peripheral vascular resistance by being innervated by a sympathetic nerve when the blood pressure rises; and the display is configured to display the video of the video signal obtained by the video signal obtainer, the waveform distortion calculated by the distortion calculator, and the fluctuations in the blood pressure of the subject measured by the measurer.

2. The biological information measuring apparatus according to claim 1, wherein:
the measurer is configured to estimate a blood pressure value corresponding to the waveform distortion calculated by the distortion calculating unit based on association information representing the waveform distortion and the blood pressure value.

3. The biological information measuring apparatus according to claim 1, wherein:
the measurer is configured to calculate a blood pressure value by multiple regression analysis using a multiple regression equation, wherein the blood pressure value of the subject is an objective variable and the waveform distortion, the heart rate, and a pulse wave amplitude of the subject are explanatory variables.

4. The biological information measuring apparatus according to claim 1, wherein:
the predetermined part of the subject is a palm.

5. A non-transitory computer-readable recording medium having stored therein a program for causing a processor having processor circuitry to function as a video signal obtainer, a video pulse wave extractor, a distortion calculator, and a measurer to execute a process for measuring biological information, the process comprising:
- obtaining a video signal of a predetermined part of a subject;
- outputting the video signal to the video signal obtainer;
- extracting, at the video pulse wave extractor, video pulse wave information representing a temporal change in a brightness value included in the video signal;
- calculating, at the distortion calculator, based on a heartbeat basic component and a second component, a waveform distortion being a change due to fluctuations in blood pressure, wherein the heartbeat basic component is obtained by filtering the extracted video pulse wave information using a filter of the distortion calculator in which the filter is set to a band corresponding to a frequency of a heartbeat of the subject and included within a range of 0.7-3.5 Hz, and the second component contains a frequency component of a frequency band higher than the heartbeat frequency band included in the video pulse information; and measuring, at the measurer, an increase of the waveform distortion as a decline of the blood pressure and measures a decrease of the waveform distortion as a rise of the blood pressure, the calculating at the distortion calculator comprises either:

an element A in a case where the waveform distortion is expressed as a difference in time between the heartbeat basic component and the second component, the element A comprising:
- detecting, at a feature point detector of the distortion calculator, a feature point of the heartbeat basic component;
- detecting, at a vertex detector of the distortion calculator, from the video pulse wave information, a vertex of an end diastolic segment of the video pulse wave; and
- calculating, at a difference calculator of the distortion calculator, as the difference in time, a time difference between the feature point and the vertex, the feature point being obtained by applying a bandpass filter to a time series signal corresponding to the video pulse wave information stored in the memory; or an element B in a case where the waveform distortion is expressed as a ratio between the heartbeat basic component and the second component in a frequency domain; the element B comprising:
- obtaining, at a convertor of the distortion calculator, a sum of Fourier coefficients of each of the heartbeat basic component and the second component; and
- calculating, at a ratio calculator of the distortion calculator, as the ratio in the frequency domain, a ratio of the sum of the Fourier coefficients of the second component to the sum of the Fourier coefficients of the heartbeat basic component;

wherein the predetermined part is a part in which an arteriole increases a peripheral vascular resistance by being innervated by a sympathetic nerve when the blood pressure rises;

the process further comprising:
displaying, at a display, a video of the video signal obtained by the video signal obtainer, the waveform distortion calculated by the distortion calculator, and the fluctuations in the blood pressure of the subject measured by the measurer.

6. A method for measuring biological information, the method comprising:
at a processor having processor circuitry being configured to function as a video signal obtainer, a video pulse wave extractor, a distortion calculator, and a measurer,
obtaining a video signal of a predetermined part of a subject;
outputting the video signal to the a-video signal obtainer;
extracting, at the video pulse wave extractor, video pulse wave information representing a temporal change in a brightness value included in the video signal;
calculating, at the distortion calculator, based on a heartbeat basic component and a second component, a waveform distortion being a change due to fluctuations in blood pressure, wherein the heartbeat basic component is obtained by filtering the extracted video pulse wave information using a filter of the distortion calculator in which the filter is set to a band corresponding to a frequency of a heartbeat of the subject and included within a range of 0.7-3.5 Hz, and the second contains a frequency component of a frequency band higher than the heartbeat frequency band included in the video pulse information; and measuring, at the measurer, an increase of the waveform distortion as a decline of the blood pressure and measuring a decrease of the waveform distortion as a rise of the blood pressure, the calculating at the distortion calculator comprises either:

an element A in a case where the waveform distortion is expressed as a difference in time between the heartbeat basic component and the second component, the element A comprising:

detecting, at a feature point detector of the distortion calculator, a feature point of the heartbeat basic component;

detecting, at a vertex detector of the distortion calculator, from the video pulse wave information, a vertex of an end diastolic segment of the video pulse wave; and calculating, at a difference calculator of the distortion calculator, as the difference in time, a time difference between the feature point and the vertex, the feature point being obtained by applying a bandpass filter to a time series signal corresponding to the video pulse wave information stored in the memory; or an element B in a case where the waveform distortion is expressed as a ratio between the heartbeat basic component and the second component in a frequency domain; the element B comprising:

obtaining, at a convertor of the distortion calculator, a sum of Fourier coefficients of each of the heartbeat basic component and the second component, and calculating, at a ratio calculator of the distortion calculator, as the ratio in the frequency domain, a ratio of the sum of the Fourier coefficients of the second component to the sum of the Fourier coefficients of the heartbeat basic component, and wherein the predetermined part is a part in which an arteriole increases a peripheral vascular resistance by being innervated by a sympathetic nerve when the blood pressure rises;

the method further comprising: displaying, at a display, a video of the video signal obtained by the video signal obtainer, the waveform distortion calculated by the distortion calculator, and the fluctuations in the blood pressure of the subject measured by the measurer.

* * * * *